(12) United States Patent
Alexander et al.

(10) Patent No.: US 10,898,330 B2
(45) Date of Patent: Jan. 26, 2021

(54) POSITIONING, DEPLOYING, AND RETRIEVING IMPLANTABLE DEVICES

(71) Applicant: Edwards Lifesciences Corporation, Irvine, CA (US)

(72) Inventors: Miles D. Alexander, Menlo Park, CA (US); Barry L Templin, Menlo Park, CA (US)

(73) Assignee: Edwards Lifesciences Corporation, Irvine, CA (US)

(*) Notice: Subject to any disclaimer, the term of this patent is extended or adjusted under 35 U.S.C. 154(b) by 315 days.

(21) Appl. No.: 15/938,814

(22) Filed: Mar. 28, 2018

(65) Prior Publication Data
US 2018/0289487 A1 Oct. 11, 2018

Related U.S. Application Data
(60) Provisional application No. 62/477,864, filed on Mar. 28, 2017.

(51) Int. Cl.
*A61F 2/24* (2006.01)
*A61B 17/34* (2006.01)
(Continued)

(52) U.S. Cl.
CPC ............ *A61F 2/2487* (2013.01); *A61B 5/029* (2013.01); *A61B 5/02028* (2013.01);
(Continued)

(58) Field of Classification Search
CPC .................... A61F 2/2487; A61B 6/02028
(Continued)

(56) References Cited

U.S. PATENT DOCUMENTS

| 3,874,388 A | 4/1975 | King et al. |
| 4,007,743 A | 2/1977 | Blake |

(Continued)

FOREIGN PATENT DOCUMENTS

| EP | 1024757 A1 | 8/2000 |
| EP | 1474032 A2 | 11/2004 |

(Continued)

OTHER PUBLICATIONS

AGA Medical Corporation. www.amplatzer.comproducts. "The Muscular VSD Occluder" and "The Septal Occluder" device description. Accessed Apr. 3, 2002.

(Continued)

*Primary Examiner* — Nadia A Mahmood
(74) *Attorney, Agent, or Firm* — Snell and Wilmer LLP

(57) ABSTRACT

Described herein are implant delivery systems and methods for controllably deploying an expandable device in a ventricle, the left atrial appendage, or other portion of the heart of a patient. In some embodiments, the implant delivery system includes means for loosening or releasing a suture on a perimeter region of the expandable device in order to control the expansion or contraction of the expandable member. In some such embodiments, loosening or releasing the suture expands the perimeter region of the expandable device to secure the expandable device in the ventricle of the patient, while tightening the suture contracts the perimeter region of the device. The system may include one or more monitoring devices to monitor aspects of the heart, such as hemodynamics.

37 Claims, 20 Drawing Sheets

(51) Int. Cl.
  *A61B 5/02* (2006.01)
  *A61F 2/958* (2013.01)
  *A61B 5/00* (2006.01)
  *A61B 5/029* (2006.01)
  *A61B 17/12* (2006.01)
  *A61M 25/10* (2013.01)
  *A61B 17/00* (2006.01)
  *A61F 2/95* (2013.01)
  *A61M 25/00* (2006.01)

(52) U.S. Cl.
  CPC ........ *A61B 5/4848* (2013.01); *A61B 17/1215* (2013.01); *A61B 17/12122* (2013.01); *A61B 17/3468* (2013.01); *A61F 2/958* (2013.01); *A61B 2017/00022* (2013.01); *A61B 2017/00292* (2013.01); *A61B 2017/00557* (2013.01); *A61B 2017/12054* (2013.01); *A61B 2505/05* (2013.01); *A61B 2560/063* (2013.01); *A61F 2002/9511* (2013.01); *A61F 2002/9583* (2013.01); *A61M 25/0074* (2013.01); *A61M 2025/1093* (2013.01)

(58) Field of Classification Search
  USPC .......................................................... 600/16
  See application file for complete search history.

(56) References Cited

U.S. PATENT DOCUMENTS

| | | |
|---|---|---|
| 4,425,908 A | 1/1984 | Simon |
| 4,453,545 A | 6/1984 | Inoue |
| 4,536,893 A | 8/1985 | Parravicini |
| 4,588,404 A | 5/1986 | Lapeyre |
| 4,619,246 A | 10/1986 | Molgaard-Nielsen et al. |
| 4,685,446 A | 8/1987 | Choy |
| 4,710,192 A | 12/1987 | Liotta et al. |
| 4,819,751 A | 4/1989 | Shimada et al. |
| 4,830,003 A | 5/1989 | Wolff et al. |
| 4,832,055 A | 5/1989 | Palestrant |
| 4,917,089 A | 4/1990 | Sideris |
| 4,983,165 A | 1/1991 | Loiterman |
| 5,104,399 A | 4/1992 | Lazarus |
| 5,192,301 A | 3/1993 | Kamiya et al. |
| 5,192,314 A | 3/1993 | Daskalakis |
| 5,258,000 A | 11/1993 | Gianturco |
| 5,375,612 A | 12/1994 | Cottenceau et al. |
| 5,385,156 A | 1/1995 | Oliva |
| 5,389,087 A | 2/1995 | Miraki |
| 5,425,744 A | 6/1995 | Fagan et al. |
| 5,433,727 A | 7/1995 | Sideris |
| 5,451,235 A | 9/1995 | Lock et al. |
| 5,496,277 A | 3/1996 | Termin et al. |
| 5,527,337 A | 6/1996 | Stack et al. |
| 5,527,338 A | 6/1996 | Purdy |
| 5,549,621 A | 8/1996 | Bessler et al. |
| 5,551,435 A | 9/1996 | Sramek |
| 5,578,069 A | 11/1996 | Miner, II |
| 5,634,936 A | 6/1997 | Linden et al. |
| 5,634,942 A | 6/1997 | Chevillon et al. |
| 5,647,870 A | 7/1997 | Kordis et al. |
| 5,702,343 A | 12/1997 | Alferness |
| 5,702,441 A | 12/1997 | Zhou |
| 5,709,707 A | 1/1998 | Lock et al. |
| 5,746,734 A | 5/1998 | Dormandy, Jr. et al. |
| 5,758,664 A | 6/1998 | Campbell et al. |
| 5,791,231 A | 8/1998 | Cohn et al. |
| 5,797,849 A | 8/1998 | Vesely et al. |
| 5,797,960 A | 8/1998 | Stevens et al. |
| 5,800,457 A | 9/1998 | Gelbfish |
| 5,800,517 A | 9/1998 | Anderson et al. |
| 5,829,447 A | 11/1998 | Stevens et al. |
| 5,833,682 A | 11/1998 | Amplatz et al. |
| 5,833,698 A | 11/1998 | Hinchliffe et al. |
| 5,836,968 A | 11/1998 | Simon et al. |
| 5,843,170 A | 12/1998 | Ahn |
| 5,860,951 A | 1/1999 | Eggers et al. |
| 5,861,003 A | 1/1999 | Latson et al. |
| 5,865,730 A | 2/1999 | Fox et al. |
| 5,865,791 A | 2/1999 | Whayne et al. |
| 5,871,017 A | 2/1999 | Mayer |
| 5,875,782 A | 3/1999 | Ferrari et al. |
| 5,876,325 A | 3/1999 | Mizuno et al. |
| 5,876,449 A | 3/1999 | Starck et al. |
| 5,879,366 A | 3/1999 | Shaw et al. |
| 5,882,340 A | 3/1999 | Yoon |
| 5,910,150 A | 6/1999 | Saadat |
| 5,916,145 A | 6/1999 | Chu et al. |
| 5,924,424 A | 7/1999 | Stevens et al. |
| 5,925,062 A | 7/1999 | Purdy |
| 5,925,076 A | 7/1999 | Inoue |
| 5,928,260 A | 7/1999 | Chin et al. |
| 5,961,440 A | 10/1999 | Schweich, Jr. et al. |
| 5,961,539 A | 10/1999 | Northrup, III et al. |
| 5,984,917 A | 11/1999 | Fleischman et al. |
| 6,024,096 A | 2/2000 | Buckberg |
| 6,024,756 A | 2/2000 | Huebsch et al. |
| 6,036,720 A | 3/2000 | Abrams et al. |
| 6,045,497 A | 4/2000 | Schweich, Jr. et al. |
| 6,059,715 A | 5/2000 | Schweich, Jr. et al. |
| 6,076,013 A | 6/2000 | Brennan et al. |
| 6,077,214 A | 6/2000 | Mortier et al. |
| 6,077,218 A | 6/2000 | Alferness |
| 6,093,199 A | 7/2000 | Brown et al. |
| 6,095,968 A | 8/2000 | Snyders |
| 6,096,347 A | 8/2000 | Geddes et al. |
| 6,099,832 A | 8/2000 | Mickle et al. |
| 6,102,887 A | 8/2000 | Altman |
| 6,125,852 A | 10/2000 | Stevens et al. |
| 6,132,438 A | 10/2000 | Fleischman et al. |
| 6,142,973 A | 11/2000 | Carleton et al. |
| 6,152,144 A | 11/2000 | Lesh et al. |
| 6,155,968 A | 12/2000 | Wilk |
| 6,156,027 A | 12/2000 | West |
| 6,161,543 A | 12/2000 | Cox et al. |
| 6,193,731 B1 | 2/2001 | Oppelt et al. |
| 6,221,092 B1 | 4/2001 | Koike et al. |
| 6,221,104 B1 | 4/2001 | Buckberg et al. |
| 6,230,714 B1 | 5/2001 | Alferness et al. |
| 6,231,561 B1 | 5/2001 | Frazier et al. |
| 6,258,021 B1 | 7/2001 | Wilk |
| 6,264,630 B1 | 7/2001 | Mickley et al. |
| 6,267,772 B1 | 7/2001 | Mulhauser et al. |
| 6,290,674 B1 | 9/2001 | Roue et al. |
| 6,296,656 B1 | 10/2001 | Bolduc et al. |
| 6,312,446 B1 | 11/2001 | Huebsch et al. |
| 6,328,727 B1 | 12/2001 | Frazier et al. |
| 6,334,864 B1 | 1/2002 | Amplatz et al. |
| 6,343,605 B1 | 2/2002 | Lafontaine |
| 6,348,068 B1 | 2/2002 | Campbell et al. |
| 6,355,052 B1 | 3/2002 | Neuss et al. |
| 6,360,749 B1 | 3/2002 | Jayaraman |
| 6,364,896 B1 | 4/2002 | Addis |
| 6,387,042 B1 | 5/2002 | Herrero |
| 6,406,420 B1 | 6/2002 | McCarthy et al. |
| 6,419,669 B1 | 7/2002 | Frazier et al. |
| 6,436,088 B2 | 8/2002 | Frazier et al. |
| 6,450,171 B1 | 9/2002 | Buckberg et al. |
| 6,482,146 B1 | 11/2002 | Alferness et al. |
| 6,482,228 B1 | 11/2002 | Norred |
| 6,506,204 B2 | 1/2003 | Mazzocchi |
| 6,508,756 B1 | 1/2003 | Kung et al. |
| 6,511,496 B1 | 1/2003 | Huter et al. |
| 6,537,198 B1 | 3/2003 | Vidlund et al. |
| 6,551,303 B1 | 4/2003 | Van Tassel et al. |
| 6,572,643 B1 | 6/2003 | Gharibadeh |
| 6,586,414 B2 | 7/2003 | Haque et al. |
| 6,592,608 B2 | 7/2003 | Fisher et al. |
| 6,613,013 B2 | 9/2003 | Haarala et al. |
| 6,622,730 B2 | 9/2003 | Ekvall et al. |
| 6,645,199 B1 | 11/2003 | Jenkins et al. |
| 6,652,555 B1 | 11/2003 | VanTassel et al. |
| 6,681,773 B2 | 1/2004 | Murphy et al. |

(56) References Cited

U.S. PATENT DOCUMENTS

| | | |
|---|---|---|
| 6,685,627 B2 | 2/2004 | Jayaraman |
| 6,702,763 B2 | 3/2004 | Murphy et al. |
| 6,730,108 B2 | 5/2004 | Van Tassel et al. |
| 6,776,754 B1 | 8/2004 | Wilk |
| 6,852,076 B2 | 2/2005 | Nikolic et al. |
| 6,887,192 B1 | 5/2005 | Whayne et al. |
| 6,951,534 B2 | 10/2005 | Girard et al. |
| 6,959,711 B2 | 11/2005 | Murphy et al. |
| 6,994,093 B2 | 2/2006 | Murphy et al. |
| 7,144,363 B2 | 12/2006 | Pai et al. |
| 7,172,551 B2 | 2/2007 | Leasure |
| 7,175,660 B2 | 2/2007 | Cartledge et al. |
| 7,279,007 B2 | 10/2007 | Nikolic et al. |
| 7,303,526 B2 | 12/2007 | Sharkey et al. |
| 7,320,665 B2 | 1/2008 | Vijay |
| 7,399,271 B2 | 7/2008 | Khairkhahan et al. |
| 7,485,088 B2 | 2/2009 | Murphy et al. |
| 7,530,998 B1 | 5/2009 | Starkey |
| 7,569,062 B1 | 8/2009 | Kuehn et al. |
| 7,582,051 B2 | 9/2009 | Khairkhahan et al. |
| 7,674,222 B2 | 3/2010 | Nikolic et al. |
| 7,758,491 B2 | 7/2010 | Buckner et al. |
| 7,762,943 B2 | 7/2010 | Khairkhahan |
| 7,824,325 B2 | 11/2010 | Dubi |
| 7,862,500 B2 | 1/2011 | Khairkhahan et al. |
| 7,887,477 B2 | 2/2011 | Nikolic et al. |
| 7,897,086 B2 | 3/2011 | Khairkhahan et al. |
| 7,938,767 B2 | 5/2011 | Evans et al. |
| 7,976,455 B2 | 7/2011 | Khairkhahan |
| 7,993,258 B2 | 8/2011 | Feld et al. |
| 8,192,478 B2 | 6/2012 | Khairkhahan et al. |
| 8,246,671 B2 | 8/2012 | Khairkhahan |
| 8,257,428 B2 | 9/2012 | Khairkhahan et al. |
| 8,377,114 B2 | 2/2013 | Khairkhahan et al. |
| 8,382,653 B2 | 2/2013 | Dubi et al. |
| 8,388,672 B2 | 3/2013 | Khairkhahan et al. |
| 8,398,537 B2 | 3/2013 | Khairkhahan et al. |
| 8,500,622 B2 | 8/2013 | Lipperman et al. |
| 8,500,790 B2 | 8/2013 | Khairkhahan |
| 8,500,795 B2 | 8/2013 | Khairkhahan et al. |
| 8,529,430 B2 | 9/2013 | Nikolic et al. |
| 8,657,873 B2 | 2/2014 | Khairkhahan et al. |
| 8,672,827 B2 | 3/2014 | Nikolic et al. |
| 8,764,848 B2 | 7/2014 | Callaghan et al. |
| 8,790,242 B2 | 7/2014 | Kermode et al. |
| 8,827,892 B2 | 9/2014 | Nikolic et al. |
| 8,931,159 B2 | 1/2015 | Hillukka |
| 9,017,394 B2 | 4/2015 | Khairkhahan |
| 9,039,597 B2 | 5/2015 | Kermode et al. |
| 9,078,660 B2 | 7/2015 | Boutillette et al. |
| 9,192,496 B2 | 11/2015 | Robinson |
| 9,332,992 B2 | 5/2016 | Alexander |
| 9,332,993 B2 | 5/2016 | Kermode et al. |
| 9,364,327 B2 | 6/2016 | Kermode et al. |
| 9,592,123 B2 | 3/2017 | Nikolic et al. |
| 10,307,147 B2 | 6/2019 | Khairkhahan et al. |
| 2001/0014800 A1 | 8/2001 | Frazier et al. |
| 2002/0019580 A1 | 2/2002 | Lau et al. |
| 2002/0026092 A1 | 2/2002 | Buckberg et al. |
| 2002/0028981 A1 | 3/2002 | Lau et al. |
| 2002/0032481 A1 | 3/2002 | Gabbay |
| 2002/0055767 A1 | 5/2002 | Forde et al. |
| 2002/0055775 A1 | 5/2002 | Carpentier et al. |
| 2002/0056461 A1 | 5/2002 | Jayaraman |
| 2002/0111647 A1 | 8/2002 | Khairkhahan et al. |
| 2002/0133227 A1 | 9/2002 | Murphy et al. |
| 2002/0161392 A1 | 10/2002 | Dubrul |
| 2002/0161394 A1 | 10/2002 | Macoviak et al. |
| 2002/0169359 A1 | 11/2002 | McCarthy et al. |
| 2002/0169360 A1 | 11/2002 | Taylor et al. |
| 2002/0183604 A1 | 12/2002 | Gowda et al. |
| 2002/0183827 A1 | 12/2002 | Derus et al. |
| 2002/0188170 A1 | 12/2002 | Santamore et al. |
| 2003/0012337 A1 | 1/2003 | Fewster et al. |
| 2003/0045896 A1 | 3/2003 | Murphy et al. |
| 2003/0050682 A1 | 3/2003 | Sharkey et al. |
| 2003/0050685 A1 | 3/2003 | Nikolic et al. |
| 2003/0057156 A1 | 3/2003 | Peterson et al. |
| 2003/0078671 A1 | 4/2003 | Lesniak et al. |
| 2003/0105384 A1 | 6/2003 | Sharkey et al. |
| 2003/0109770 A1 | 6/2003 | Sharkey et al. |
| 2003/0120337 A1 | 6/2003 | Van Tassel et al. |
| 2003/0135230 A1 | 7/2003 | Massey et al. |
| 2003/0149333 A1 | 8/2003 | Alferness |
| 2003/0149422 A1 | 8/2003 | Muller |
| 2003/0158570 A1 | 8/2003 | Ferrazzi |
| 2003/0181928 A1 | 9/2003 | Vidlund et al. |
| 2003/0181942 A1 | 9/2003 | Sutton et al. |
| 2003/0212429 A1 | 11/2003 | Keegan et al. |
| 2003/0220667 A1 | 11/2003 | van der Burg et al. |
| 2003/0225445 A1 | 12/2003 | Derus et al. |
| 2003/0229265 A1 | 12/2003 | Girard et al. |
| 2004/0002626 A1 | 1/2004 | Feld et al. |
| 2004/0034366 A1 | 2/2004 | van der Burg et al. |
| 2004/0044361 A1 | 3/2004 | Frazier et al. |
| 2004/0049210 A1 | 3/2004 | VanTassel et al. |
| 2004/0054394 A1 | 3/2004 | Lee |
| 2004/0064014 A1 | 4/2004 | Melvin et al. |
| 2004/0122090 A1 | 6/2004 | Lipton |
| 2004/0127935 A1 | 7/2004 | VanTassel et al. |
| 2004/0133062 A1 | 7/2004 | Pai et al. |
| 2004/0136992 A1 | 7/2004 | Burton et al. |
| 2004/0172042 A1 | 9/2004 | Suon et al. |
| 2004/0186511 A1 | 9/2004 | Stephens et al. |
| 2004/0215230 A1 | 10/2004 | Frazier et al. |
| 2004/0220610 A1 | 11/2004 | Kreidler et al. |
| 2004/0243170 A1 | 12/2004 | Suresh et al. |
| 2004/0260331 A1 | 12/2004 | D'Aquanni et al. |
| 2004/0260346 A1 | 12/2004 | Overall et al. |
| 2004/0267086 A1 | 12/2004 | Anstadt et al. |
| 2004/0267378 A1 | 12/2004 | Gazi et al. |
| 2005/0007031 A1 | 1/2005 | Hyder |
| 2005/0015109 A1 | 1/2005 | Lichtenstein |
| 2005/0038470 A1 | 2/2005 | van der Burg et al. |
| 2005/0043708 A1 | 2/2005 | Gleeson et al. |
| 2005/0065548 A1 | 3/2005 | Marino et al. |
| 2005/0085826 A1 | 4/2005 | Nair et al. |
| 2005/0096498 A1 | 5/2005 | Houser et al. |
| 2005/0113811 A1 | 5/2005 | Houser et al. |
| 2005/0113861 A1 | 5/2005 | Corcoran et al. |
| 2005/0124849 A1 | 6/2005 | Barbut et al. |
| 2005/0137690 A1 | 6/2005 | Salahieh et al. |
| 2005/0142180 A1 | 6/2005 | Bisgaier et al. |
| 2005/0154252 A1 | 7/2005 | Sharkey et al. |
| 2005/0177180 A1 | 8/2005 | Kaganov et al. |
| 2005/0187620 A1 | 8/2005 | Pai et al. |
| 2005/0197716 A1 | 9/2005 | Sharkey et al. |
| 2005/0216052 A1 | 9/2005 | Mazzocchi et al. |
| 2005/0228434 A1 | 10/2005 | Amplatz et al. |
| 2005/0256532 A1 | 11/2005 | Nayak et al. |
| 2005/0277981 A1 | 12/2005 | Maahs et al. |
| 2005/0277983 A1 | 12/2005 | Saadat et al. |
| 2005/0283218 A1 | 12/2005 | Williams |
| 2006/0014998 A1 | 1/2006 | Sharkey et al. |
| 2006/0019888 A1 | 1/2006 | Zhou |
| 2006/0025800 A1 | 2/2006 | Suresh |
| 2006/0030881 A1 | 2/2006 | Sharkey et al. |
| 2006/0063970 A1 | 3/2006 | Raman et al. |
| 2006/0069430 A9 | 3/2006 | Randert et al. |
| 2006/0079736 A1 | 4/2006 | Chin et al. |
| 2006/0116692 A1 | 6/2006 | Ward |
| 2006/0135947 A1 | 6/2006 | Soltesz et al. |
| 2006/0136043 A1 | 6/2006 | Cully et al. |
| 2006/0167334 A1 | 7/2006 | Anstadt et al. |
| 2006/0173524 A1 | 8/2006 | Salahieh et al. |
| 2006/0199995 A1 | 9/2006 | Vijay |
| 2006/0229491 A1 | 10/2006 | Sharkey et al. |
| 2006/0241334 A1 | 10/2006 | Dubi et al. |
| 2006/0259124 A1 | 11/2006 | Matsuoka et al. |
| 2006/0264980 A1 | 11/2006 | Khairkhahan et al. |
| 2006/0276684 A1 | 12/2006 | Speziali |
| 2006/0281965 A1* | 12/2006 | Khairkhahan ... A61B 17/12022 600/37 |
| 2007/0129753 A1 | 6/2007 | Quinn et al. |

(56) References Cited

U.S. PATENT DOCUMENTS

| | | | |
|---|---|---|---|
| 2007/0135826 A1 | 6/2007 | Zaver et al. |
| 2007/0135889 A1 | 6/2007 | Moore et al. |
| 2007/0161846 A1 | 7/2007 | Nikolic et al. |
| 2007/0162048 A1 | 7/2007 | Quinn et al. |
| 2007/0213578 A1 | 9/2007 | Khairkhahan et al. |
| 2007/0213815 A1 | 9/2007 | Khairkhahan et al. |
| 2007/0270931 A1 | 11/2007 | Leanna et al. |
| 2008/0015717 A1 | 1/2008 | Griffin et al. |
| 2008/0045778 A1 | 2/2008 | Lichtenstein et al. |
| 2008/0071133 A1 | 3/2008 | Dubi |
| 2008/0071134 A1 | 3/2008 | Dubi et al. |
| 2008/0221384 A1 | 9/2008 | Chi Sing et al. |
| 2008/0228205 A1 | 9/2008 | Sharkey et al. |
| 2008/0293996 A1 | 11/2008 | Evans et al. |
| 2008/0300672 A1 | 12/2008 | Kassab et al. |
| 2008/0319254 A1 | 12/2008 | Nikolic et al. |
| 2009/0054723 A1 | 2/2009 | Khairkhahan et al. |
| 2009/0062601 A1 | 3/2009 | Khairkhahan et al. |
| 2009/0112050 A1 | 4/2009 | Farnan et al. |
| 2009/0187063 A1 | 7/2009 | Khairkhahan |
| 2009/0228093 A1 | 9/2009 | Taylor et al. |
| 2010/0022821 A1 | 1/2010 | Dubi et al. |
| 2010/0030256 A1 | 2/2010 | Dubrul et al. |
| 2010/0057185 A1 | 3/2010 | Melsheimer et al. |
| 2010/0121132 A1 | 5/2010 | Nikolic et al. |
| 2010/0274227 A1 | 10/2010 | Khairkhahan et al. |
| 2011/0021864 A1 | 1/2011 | Criscione et al. |
| 2011/0046712 A1 | 2/2011 | Melsheimer et al. |
| 2011/0092761 A1 | 4/2011 | Almog et al. |
| 2011/0098525 A1 | 4/2011 | Kermode et al. |
| 2011/0178362 A1 | 7/2011 | Evans et al. |
| 2011/0257461 A1 | 10/2011 | Lipperman et al. |
| 2011/0264204 A1 | 10/2011 | Khairkhahan |
| 2012/0041257 A1 | 2/2012 | Stankus et al. |
| 2012/0245604 A1 | 9/2012 | Tegzes |
| 2012/0330408 A1 | 12/2012 | Hillukka et al. |
| 2013/0090677 A1 | 4/2013 | Evans et al. |
| 2013/0165735 A1 | 6/2013 | Khairkhahan et al. |
| 2013/0274595 A1 | 10/2013 | Kermode et al. |
| 2014/0180271 A1 | 6/2014 | Johnson et al. |
| 2014/0296624 A1 | 10/2014 | Kermode et al. |
| 2014/0343356 A1 | 11/2014 | Nikolic et al. |
| 2014/0345109 A1 | 11/2014 | Grant et al. |
| 2014/0364941 A1 | 12/2014 | Edmiston et al. |
| 2014/0371789 A1 | 12/2014 | Hariton et al. |
| 2015/0209144 A1 | 7/2015 | Khairkhahan |
| 2015/0265405 A1 | 9/2015 | Boutillette et al. |
| 2015/0297381 A1 | 10/2015 | Essinger et al. |
| 2016/0262892 A1 | 9/2016 | Kermode et al. |
| 2016/0302924 A1 | 10/2016 | Boutillette et al. |

FOREIGN PATENT DOCUMENTS

| | | |
|---|---|---|
| EP | 2082690 B1 | 6/2012 |
| JP | H08257031 A | 10/1996 |
| KR | 101070811 B1 | 10/2011 |
| WO | 9803213 A1 | 1/1998 |
| WO | 0230335 A2 | 4/2002 |
| WO | 02087481 A1 | 11/2002 |
| WO | 03103743 A1 | 12/2003 |
| WO | 2004012629 A1 | 2/2004 |
| WO | 2008010792 A1 | 1/2008 |
| WO | 2011041422 A2 | 4/2011 |
| WO | 2012099418 A2 | 7/2012 |
| WO | 2013065036 A2 | 5/2013 |
| WO | 0245710 A1 | 6/2020 |

OTHER PUBLICATIONS

Anand et al.; Isolated myocyte contractile function is normal in postinfarct remodeled rat heart with systolic dysfunction; Circulation ; 96(11); pp. 3974-3984; Dec. 1997.

Artrip et al.; Left ventricular volume reduction surgery for heart failure: A physiologic perspective; J Thorac Cardiovasc Surg; vol. 122; No. 4; pp. 775-782; Oct. 2001.

Boersma et al.; Early thrombolytic treatment in acute myocardial infarction: reappraisal of the golden hour; Lancet: vol. 348(9030); pp. 771-775; Sep. 21, 1996.

Bozdag-Turan et al.; Left ventricular partitioning device in a patient with chronic heart failure: Short-term clinical follow-up; Int J Cardiol; 163(1); pp. e1-e3; (Epub) Jul. 2012.

Dang et al.; Akinetic myocardial infarcts must contain contracting myocytes: finite-element model study; Am J Physiol Heart Circ Physiol ; 288; pp. H1844-H1850; Apr. 2005.

Dang et al.; Effect of ventricular size and patch stiffness in surgical anterior ventricular restoration: a finite element model study; Ann Thorac Surg; 79; pp. 185-193; Jan. 2005.

Di Mattia et al. Surgical treatment of left ventricular post-infarction aneurysm with endoventriculoplasty: late clinical and functioal results. European Journal of Cardio-thoracic Surgery. 15(4):413-418; Apr. 1999.

Dor et al. Ventricular remodeling in coronary artery disease. Current Opinion in Cardiology. 12(6):533-537; Nov. 1997.

Dor V. The treatment of refractory ischemic ventricular tachycardia by endoventricular patch plasty reconstruction of the left ventricle. Seminars in Thoracic and Cardiovascular Surgery. 9(2): 146-155; Apr. 1997.

Dor. Surgery for left ventricular aneurysm. Current Opinion in Cardiology. vol. 5; No. 6; pp. 773-780; Dec. 1990.

Gore Medical. www.goremedical.com. "Helex Septal Occluder" product description. Accessed Apr. 3, 2002.

Grossman et al.; Wall stress and patterns of hypertrophy in the human left ventricle; J Clin Invest; 56; pp. 56-64; Jul. 1975.

Guccione et al.; Finite element stress analysis of left ventricular mechanics in the beating dog heart; J Biomech; 28; pp. 1167-1177; Oct. 1995.

Guccione et al.; Mechanics of active contraction in cardiac muscle: Part II—Cylindrical models of the systolic left ventricle; J Biomech Eng; 115; pp. 82-90; Feb. 1993.

Gutberlet et al.; Myocardial viability assessment in patients with highly impaired left ventricular function: comparison of delayed enhancement dobutamine stress MRI end-diastolic wall thickness and TI201-SPECT with functional recovery after revascularization; Eur Radiol; 15; pp. 872-880; May 2005.

Huisman et al.; Measurement of left ventricular wall stress; Cardiovascular Research; 14; pp. 142-153; Mar. 1980.

Jackson et al.; Extension of borderzone myocardium in postinfarction dilated cardiomyopathy; J Am Coll Cardiol; 40(6);1160-7; and discussion; pp. 1168-1171; Sep. 2002.

James et al.; Blood volume and Brain Natriuretic Peptide in Congestive Heart Failure: A Pilot Study; American Heart Journal; vol. 150; issue 5 pp. 984.e1-984.e6 (abstract); Dec. 6, 2005.

Januzzi James L.; Natriuretic peptide testing: A window into the diagnosis and prognosis of heart failure; Cleveland Clinic Journal of Medicine; vol. 73; No. 2; pp. 149-152 and 155-157; Feb. 2006.

Jones et al.; Coronary Bypass Surgery with or without Surgical Ventricular Reconstruction; N Engl J Med; 360; pp. 1705-1717; Apr. 2009.

Katsumata et al. An objective appraisal of partial left ventriculectomy for heart failure. Journal of Congestive Heart Failure and Circulator Support. 1(2): 97-106; (month unavailable) 1999.

Kawata et al. Systolic and Diastolic Function after Patch Reconstruction of Left Ventricular Aneurysms. Ann. Thorac. Surg. 5(2)9:403-407; Feb. 1995.

Lee et al.; A novel method for quantifying in-vivo regional left ventricular myocardial contractility in the border zone of a myocardial infarction (author manuscript 11 pgs.); J Biomech Eng; 133; 094506; Sep. 2011.

Mazzaferri et al.; Percutaneous left ventricular partitioning in patients with chronic heart failure and a prior anterior myocardial infarction: Results of the Percutaneous Ventricular Restoration in Chronic Heart Failure Patients Trial; Am Heart J; 163; pp. 812-820; May 2012.

Nikolic et al.; Percutaneous implantation of an intraventricular device for the treatment of heart failure: experimental results and proof of concept; J Card Fail; 15(9); pp. 790-797; Nov. 2009.

(56) References Cited

OTHER PUBLICATIONS

Prakash Sojitra et al, "Electropolishing of 316LVM Stainless Steel Cardiovascular Stents: An Investigation of Material Removal, Surface Roughness and Corrosion Behaviour," Trends Biomater. Artif. Organs, vol. 23(3), pp. 115-121 Jan. (2010).

Priola et al.; Functional characteristics of the left ventricular inflow and outflow tracts; Circ Res; 17; pp. 123-129; Aug. 1965.

Sagic et al.; Percutaneous implantation of the left ventricular partitioning device for chronic heart failure: a pilot study with 1-year follow-up. Eur J Heart Fail; 12; pp. 600-606; Apr. 2010.

Sharkey et al.; Left ventricular apex occluder. Description of a a ventricular partitioning device; EuroInterv.; 2(1); pp. 125-127; May 2006.

Sojitra et al.; Electropolishing of 316LVM stainless steel cardiovascular stents: an investigation of material removal surface roughness and corrosion behaviour; Trends Biomater. Artif. Organs; 23(3); pp. 115-121; (month available) 2010.

Sun et al.; A computationally efficient formal optimization of regional myocardial contractility in a sheep with left ventricular aneurysm (author manuscript 21 pgs.); J Biomech Eng; 131; 111001; Nov. 2009.

U.S. Food & Drug Administration; AneuRx Stent Graft System-Instructions for use; (pre-market approval); Sep. 29, 1999; downloaded Apr. 25, 2013 (http:www.accessdata.fda.govcdrh_docspdfP990020c.pdf).

Walker et al; Magnetic resonance imaging-based finite element stress analysis after linear repair of left ventricular aneurysm (author manuscript 17 pgs.); J Thorac Cardiovasc Surg; 135; pp. 1094-1102 e1-2; May 2008.

Walker et al; MRI-based finite-element analysis of left ventricular aneurysm; Am J Physiol Heart Circ Physiol; 289; pp. H1692-H700; Aug. 2005.

Walmsley; Anatomy of left ventricular outflow tract; British Heart Journal; 41; pp. 263-267; Mar. 1979.

Wenk et al.; First evidence of depressed contractility in the border zone of a human myocardial infarction; Ann Thorac Surg; 93; pp. 1188-1193; Apr. 2012.

Wenk et al.; Regional left ventricular myocardial contractility and stress in a finite element model of posterobasal myocardial infarction (author manuscript pgs.); J Biomech Eng; 133(4); 044501; Apr. 2011.

\* cited by examiner

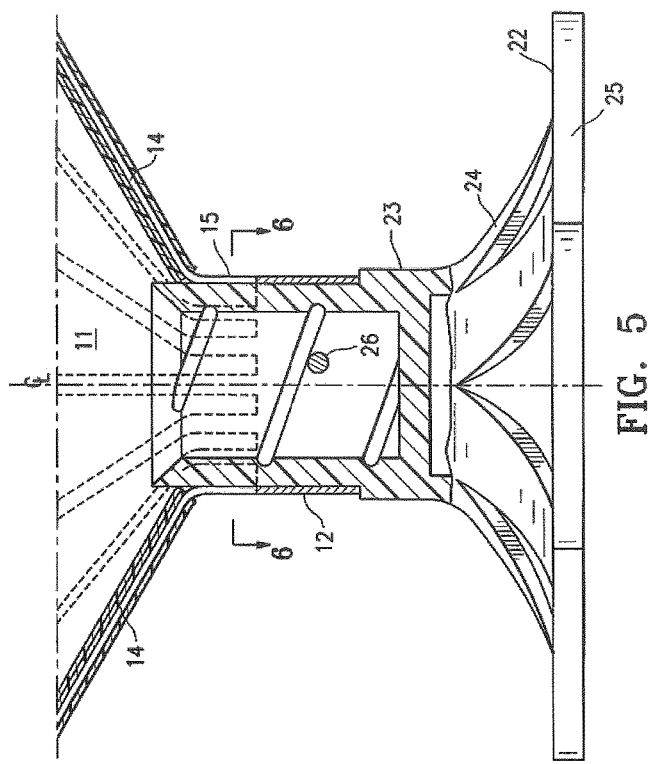
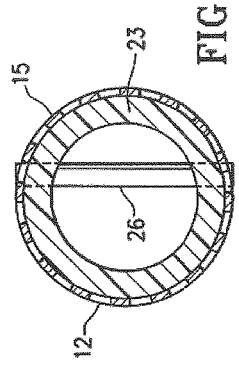
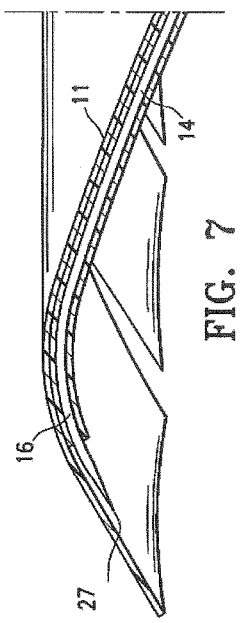
FIG. 5
FIG. 6
FIG. 7

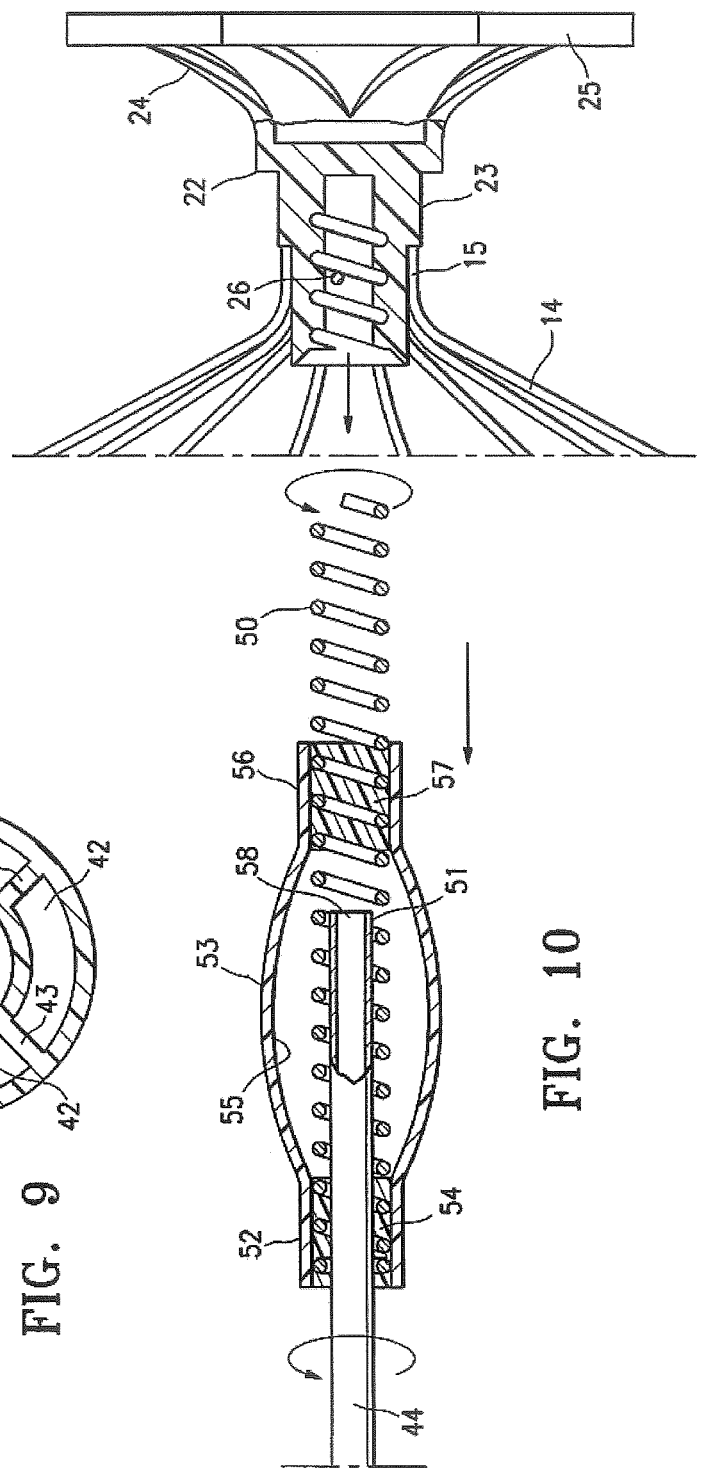

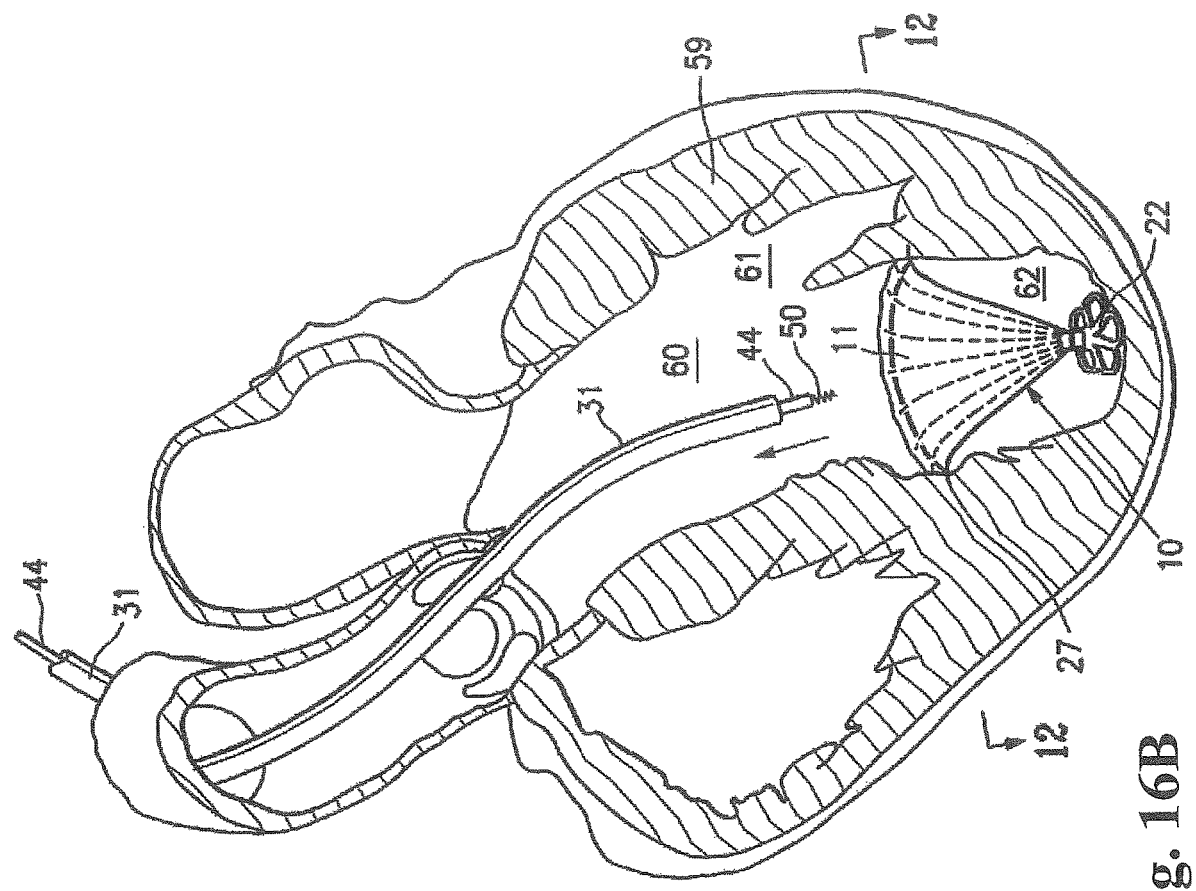
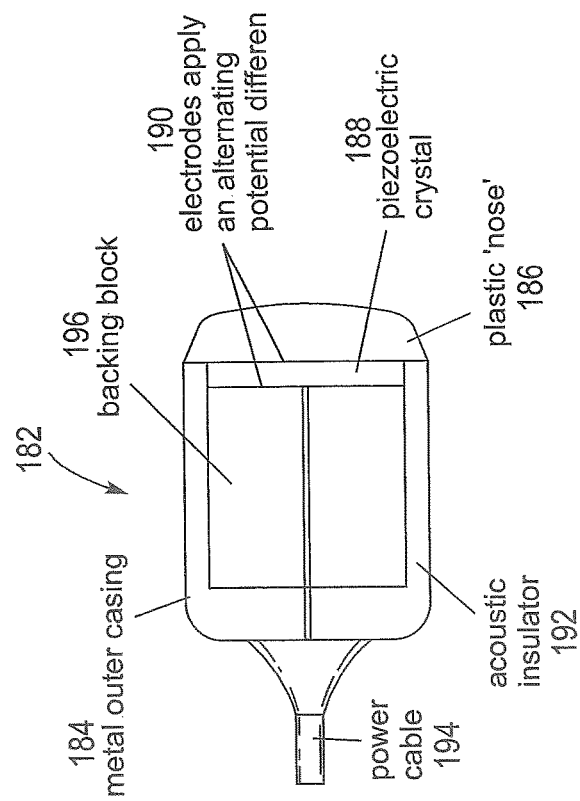
Fig. 16A
Fig. 16B

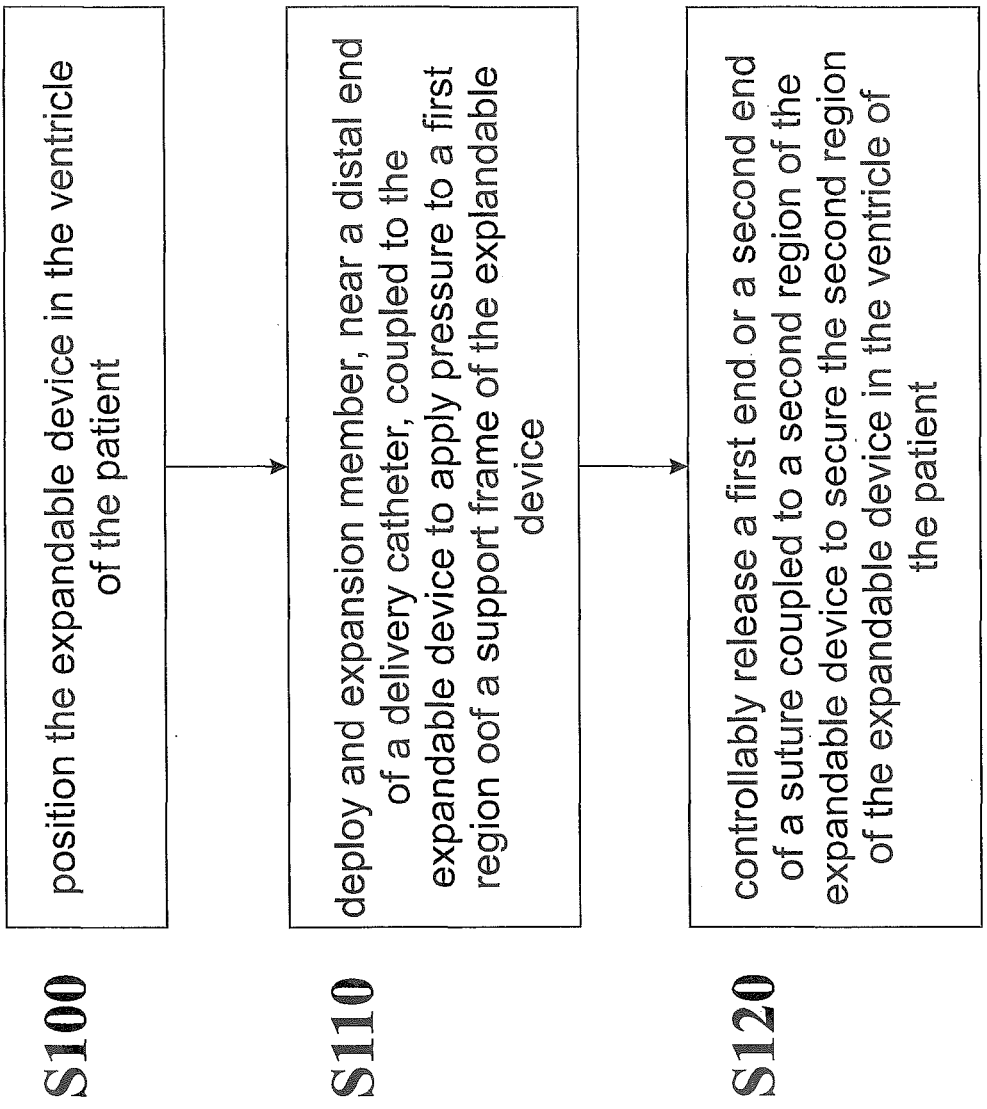

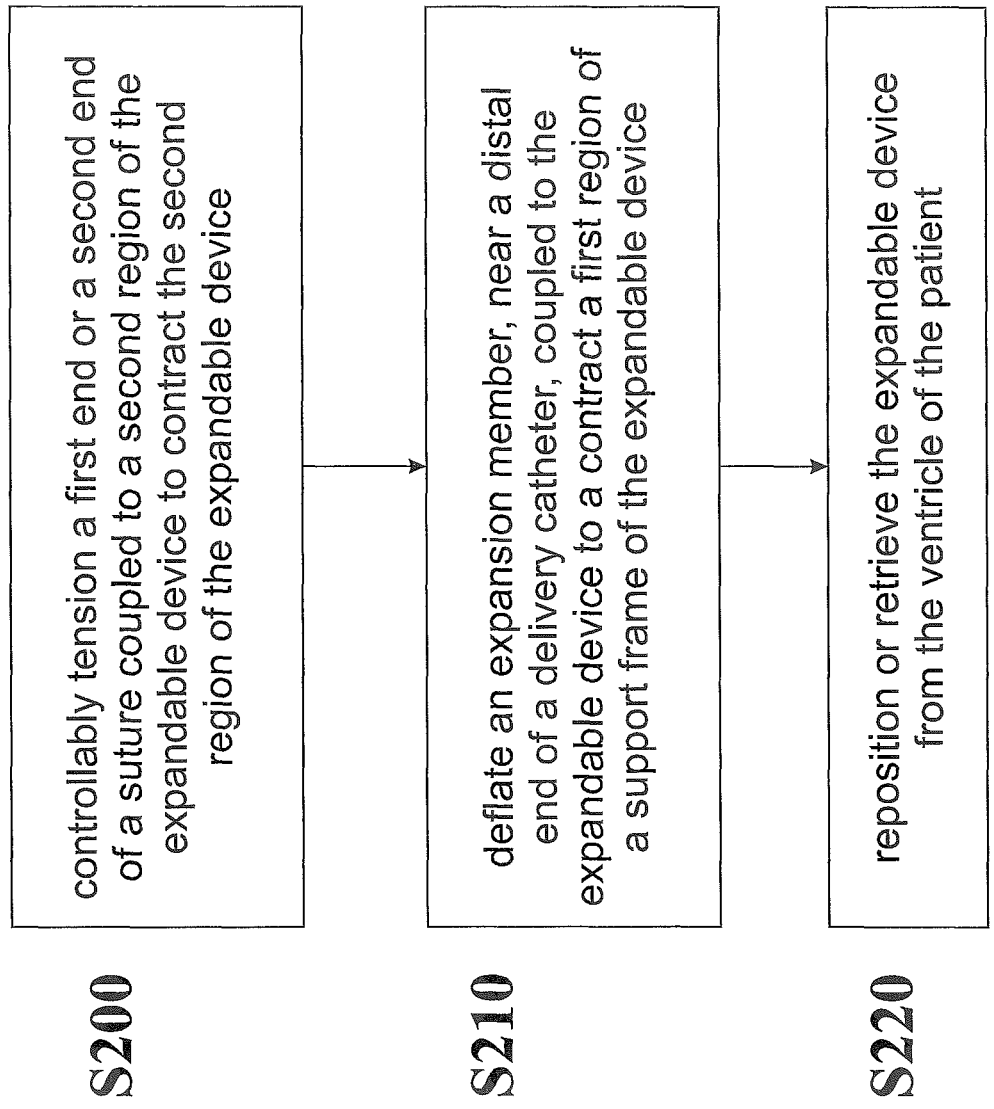

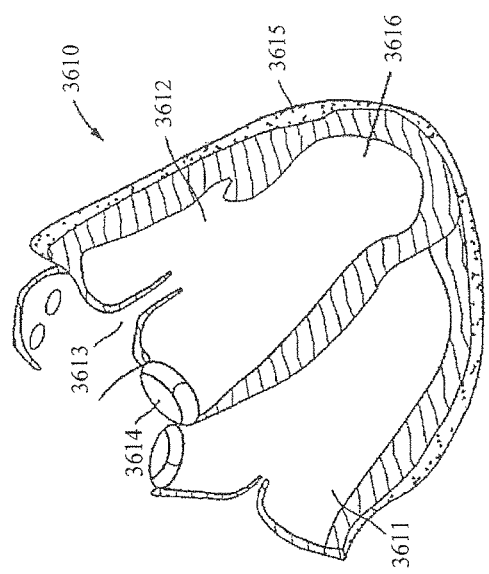
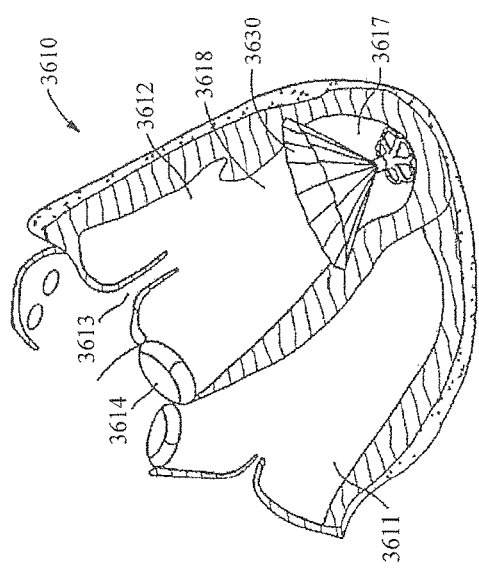
FIG. 20A
FIG. 20B

POSITIONING, DEPLOYING, AND RETRIEVING IMPLANTABLE DEVICES

INCORPORATION BY REFERENCE

This application claims priority to U.S. Provisional Application Ser. No. 62/477,864, filed Mar. 28, 2017, the disclosure of which is incorporated herein by reference.

TECHNICAL FIELD

This invention relates generally to the medical/surgical devices field and methods pertaining to treating heart disease. More specifically, the present invention relates to devices and methods for delivering an expandable device to a patient's ventricle or other location in the heart.

BACKGROUND

Described herein are systems, methods, and devices for improving cardiac function, and, in general, treating heart disease, particularly heart failure. More specifically, described herein are systems, methods, and devices for delivering an expandable device to a patient's ventricle.

Heart failure annually leads to millions of hospital visits internationally. Heart failure (including congestive heart failure) is the description given to a myriad of symptoms that can be the result of the heart's inability to meet the body's demand for blood flow. In certain pathological conditions, the ventricles of the heart become ineffective in pumping the blood, causing a back-up of pressure in the vascular system behind the ventricle.

The reduced effectiveness of the heart is usually due to an enlargement of the heart. A myocardial ischemia may, for example, cause a portion of a myocardium of the heart to lose its ability to contract. Prolonged ischemia can lead to infarction of a portion of the myocardium (heart muscle) wherein the heart muscle dies and becomes scar tissue. Once this tissue dies, it no longer functions as a muscle and cannot contribute to the pumping action of the heart. When the heart tissue is no longer pumping effectively, that portion of the myocardium is said to be hypokinetic, meaning that it is less contractile than the uncompromised myocardial tissue. As this situation worsens, the local area of compromised myocardium may in fact bulge out as the heart contracts, further decreasing the heart's ability to move blood forward. When local wall motion moves in this way, it is said to be dyskinetic, or akinetic. The dyskinetic portion of the myocardium may stretch and eventually form an aneurysmic bulge. Certain diseases may cause a global dilated myopathy, i.e., a general enlargement of the heart when this situation continues for an extended period of time.

As the heart begins to fail, diastolic pressures increase, which stretches the ventricular chamber prior to contraction and greatly increases the pressure in the heart. In response, the heart tissue reforms to accommodate the chronically increased filling pressures, further increasing the work that the now compromised myocardium must perform.

Drug therapy typically treats the symptoms of the disease and may slow the progression of the disease, but it cannot cure the disease. One of the only permanent treatments for heart failure is heart transplantation, but heart transplant procedures are very risky, extremely invasive and expensive, and are performed on only a small percentage of patients. Many patients do not qualify for heart transplant for failure to meet any one of a number of qualifying criteria, and, furthermore, there are not enough hearts available for transplant to meet the needs of HF patients who do qualify.

Substantial effort has been made to find alternative treatments for heart failure. For example, surgical procedures have been developed to dissect and remove weakened portions of the ventricular wall in order to reduce heart volume. This procedure is highly invasive, risky and expensive and is commonly only done in conjunction with other procedures (such as heart valve replacement or coronary artery by-pass graft). Additionally, the surgical treatment is usually only offered to the most severe class of patients and, accordingly, is not an option for most patients facing ineffective drug treatment. Finally, if the procedure fails, emergency heart transplant is the only presently available option.

Ventricular expandable devices offer a solution for treating heart failure. These devices generally function to partition a patient's ventricle into a productive region and a non-productive region. For such devices to function properly, they are positioned in a specific location within the patient's heart chamber. Delivery of an expandable device may be made complicated by the anatomy of a patient and by aspects or characteristics of the delivery device or expandable device itself.

Further background may be found in U.S. Pat. Nos. 7,582,051 & 8,398,537 (Khairkahan et al), which are entitled "Peripheral seal for a ventricular partitioning device" and which are both incorporated by reference herein.

Thus, there is a need for new and useful devices, systems, and methods for delivering, deploying, and, if necessary, repositioning an expandable device in a patient's ventricle. This invention provides such new and useful devices, systems, and methods.

SUMMARY OF THE INVENTION

In one embodiment, an implant delivery system for controllably deploying an expandable partitioning device in a ventricle of a patient has a delivery catheter with a proximal end, a distal end, and a tubular shaft therebetween. The system also includes an expandable device that has a support frame with radially expandable resilient ribs connected at their distal ends to a central hub. A membrane is coupled to the ribs.

A suture extends around a periphery of the membrane, preferably at a proximal region or end of the expandable device, although it may be located elsewhere on the device. The suture is adapted to be loosened to expand a perimeter region of the expandable device to secure the expandable device in a ventricle of the patient. An expansion member near the distal end of the delivery catheter is configured to apply pressure to a distal region of a support frame of the expandable device to expand the distal region of the support frame. A coupling element is configured to secure the expansion member to the expandable device during deployment.

The suture is adapted to be tightened to contract the expandable device and to be loosened to permit the expandable device to expand. In one embodiment, at least one end of the suture extends through the tubular shaft and out a proximal end of the delivery catheter.

Embodiments herein may have one or more optional features, which may be incorporated alone or in combinations. The suture may be removable from the membrane. The expansion member may be, for example, an inflatable balloon. Ends of the suture may be secured together, or may be unsecured. A diagnostic instrument may be integrated into the delivery system to measure hemodynamics of the heart. The expandable device may optionally include a foot for contacting a first interior wall portion of a heart.

In another embodiment, an implant delivery system controllably deploys an expandable device in a ventricle of a patient. The system includes a delivery catheter having a proximal end, a distal end, and a tubular shaft therebetween. The system also includes an expandable device comprising a support frame having radially expandable ribs connected at their distal ends to a central hub, and a membrane coupled to said ribs, wherein said ribs are adapted to anchor to a wall of a ventricle of the heart. A suture extends around the periphery of the membrane and is adapted to be loosened to expand a perimeter region of the expandable device. This secures the expandable device in a ventricle of the patient. Optionally, at least one end of the suture may extend through the tubular shaft and out a proximal end of the delivery catheter.

Various features may be incorporated, either individually or in combination. The support frame may, for example, be self-expanding. The suture may be adapted to releasably restrain expansion of the expandable device. The system may include an implant expansion member to apply pressure to a distal region of a support frame. A coupling element secures the expansion member to the expandable device during deployment. Further, the suture may be adapted to be tightened to contract the expandable device.

In another embodiment, an implant delivery system is provided for controllably deploying an expandable device in a ventricle or left atrial appendage of a patient. The system includes a delivery catheter having a proximal end, a distal end, and a tubular shaft therebetween. An expandable device has a support frame with a membrane coupled thereto. A strand extends around the periphery of the membrane. The strand is adapted to be loosened to expand a perimeter region of the expandable device to secure the expandable device against a wall in a portion of the heart of the patient.

Embodiments may include one or more optional features, which may be incorporated individually or in combinations. The strand may be removable from the membrane. The strand may be a suture, for example, although it may take other forms that serve to allow the structure to expand when the strand is loosened. The membrane may be impermeable to blood as when, for example, a portion of the ventricle is to be partitioned or when the left atrial appendage is to be sealed.

The system may further include an expansion member such as, for example, an inflatable balloon. The expansion member may be located near the distal end of the delivery catheter and configured to apply pressure to a distal region of a support frame of the expandable device to expand the distal region of the support frame. The suture may be located in a proximal region of the expandable device, such that the expansion member serves to expand a distal portion of the device and the suture controls expansion of a proximal portion of the device. A coupling element may be provided to secure the expansion member to the expandable device during deployment.

Continuing with other optional features that may be present in embodiments of the present invention, either alone or in combination, the support frame may be self-expanding. An end of the strand may be adapted to be pulled to remove the strand from the periphery of the membrane. The system may include a hypotube on the distal end of the delivery catheter, at least one end of the strand extending into the hypotube. The hypotube may have a slot for receiving the suture of the expandable device.

At least one end of the strand may extend through the tubular shaft and out a proximal end of the delivery catheter. Alternatively, both ends of the strand are threaded through the tubular shaft of the delivery catheter. The strand may be adapted to be tightened to contract the expandable device and to be loosened to permit the expandable device to expand. In one arrangement, a clamp is provided on a distal end of the delivery catheter, with at least one end of the strand being secured to the clamp.

The system may optionally include a diagnostic instrument integrated into the delivery system that measures hemodynamics in the heart.

Another aspect of the invention includes a method for controllably deploying an expandable device in a ventricle of a patient. The expandable device is positioned in the ventricle of the patient. An expansion member is provided near a distal end of a delivery catheter of a delivery system, coupled to the expandable device to apply pressure to a region of a support frame of the expandable device. Applying pressure to the region of the support frame expands the region of the support frame. An end of a suture is coupled to the expandable device to secure the expandable device in the ventricle of the patient, Controllably releasing the end of the suture causes increased outward expansive force of the expandable device and securing the device against the wall of the ventricle. In this method, deploying and releasing may optionally occur simultaneously. Optionally, the expansion member may expand a distal region of the device while the suture controls expansion of a proximal region of the device.

The present invention also extends to a method of monitoring blood flow dynamics in a ventricle during positioning of an expandable device in the ventricle, The method includes measuring baseline hemodynamics, positioning the expandable device in the ventricle, measuring a second set of hemodynamics in the ventricle; and repositioning the expandable device based on the hemodynamic measurements.

A further understanding of the nature and advantages of the present invention are set forth in the following description and claims, particularly when considered in conjunction with the accompanying drawings.

BRIEF DESCRIPTION OF THE DRAWINGS

FIG. 5 is a partial cross-sectional view of the hub of the expandable device shown in FIG. 2 taken along the lines 5-5.

FIG. 6 is a transverse cross sectional view of the hub shown in FIG. 5 taken along the lines 6-6.

FIG. 7 is a longitudinal view, partially in section of a reinforcing rib and membrane at the periphery of the expandable device shown in FIG. 1.

FIG. 9 is a transverse cross-sectional view of the delivery system shown in FIG. 8 taken along the lines 9-9.

FIG. 10 is an elevational view, partially in section, of the hub shown in FIG. 5 being secured to the coupling element of the delivery system shown in FIG. 8.

FIG. 11A is a schematic view of the expandable device of FIGS. 1 and 2, illustrating the device being delivered through the delivery system to the heart chamber, the delivery system comprising a guide catheter and a delivery catheter. FIG. 11B is a schematic view of the expandable device, illustrating the device being held in place while the guide catheter is withdrawn. FIG. 11C is a schematic view of the expandable device in a collapsed configuration in the heart chamber. FIG. 11D is a schematic view of the expandable device, illustrating expansion of the second region of the device in the heart chamber. FIG. 11E is a schematic view of the expandable device positioned in the heart chamber. FIG. 11F is a schematic view of the expandable device in the heart chamber, illustrating removal of the delivery system from the expandable device.

FIGS. 16A and 16B are schematic views of a device positioning system.

FIG. 17 is a flow chart illustrating a method of positioning an expandable device.

FIG. 18 is a flow chart illustrating a method of repositioning or retrieving an expandable device.

FIGS. 20A-20B are schematic views of a ventricle with an expandable device positioned therein.

DETAILED DESCRIPTION

The following description of the embodiments of the invention is not intended to limit the invention to these embodiments, but rather to enable any person skilled in the art to make and use this invention. Disclosed herein are devices, systems, and methods for positioning, deploying, and retrieving implantable devices.

Described herein are deployable and retrievable cardiac treatment devices or implants, systems including retrievable devices, and methods of using them. For example, any of the implants described herein may be positioned in a patient's heart (and particularly the patient's ventricle, such as the left ventricle), deployed in the heart by expanding the device, and then, either immediately or after some time period, disengaged from the heart, at least partially collapsed, and repositioned and/or removed. The implants, which may also be referred to as cardiac treatment devices, may be configured to partition the heart (e.g., into a productive and non-productive region), or to support the wall of the heart. Examples of such implants are described herein. Systems and methods for deploying and/or retrieving any of the implants described herein are also taught.

Devices and Systems

Figure 1:
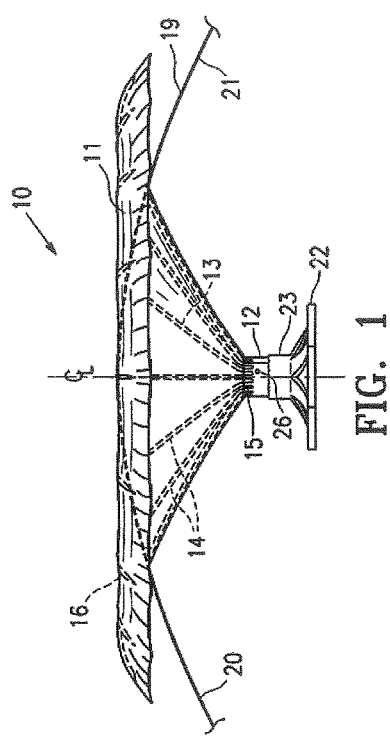
FIG. 1 is an elevational view of an expandable device embodying features of the invention in an expanded configuration.

FIGS. 1-4 illustrate an expandable device 10 including a membrane 11, a hub 12, for example centrally located on the expandable device, a support component or foot 22, and a radially expandable reinforcing frame 13 is secured to the proximal or pressure side of the frame 13 as shown in FIG. 1. The ribs 14 have second ends 15 which are secured to the hub 12 and free first ends 16 which are configured to curve or flare away from a center line axis. Radial expansion of the first free ends 16 unfurls the membrane 11 secured to the frame 13 so that the membrane presents a pressure receiving surface 17, which defines in part the productive portion of the patient's partitioned heart chamber.

In some embodiments, the membrane 11 may be formed of suitable biocompatible polymeric material which includes ePTFE (expanded polytetrafluoroethylene), Nylon, PET (polyethylene terephthalate), and polyesters such as Hytrel. The membrane 11 may be foraminous in nature to facilitate tissue ingrowth after deployment within the patient's heart. The delivery catheter 32 and the guide catheter 31 may be formed of suitable high strength polymeric material such as PEEK (polyetheretherketone), polycarbonate, PET, Nylon, and the like. Braided composite shafts may also be employed.

Figure 4:
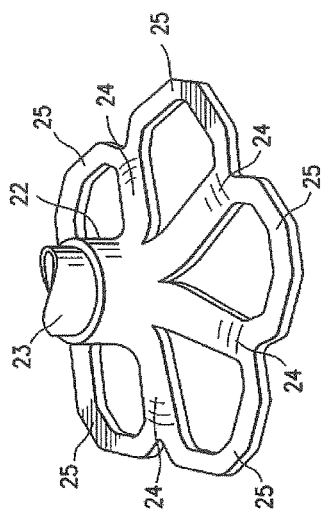
FIG. 4 is a perspective view of the non-traumatic support component of the distally extending stem of the device shown in FIG. 1.
Figure 8:
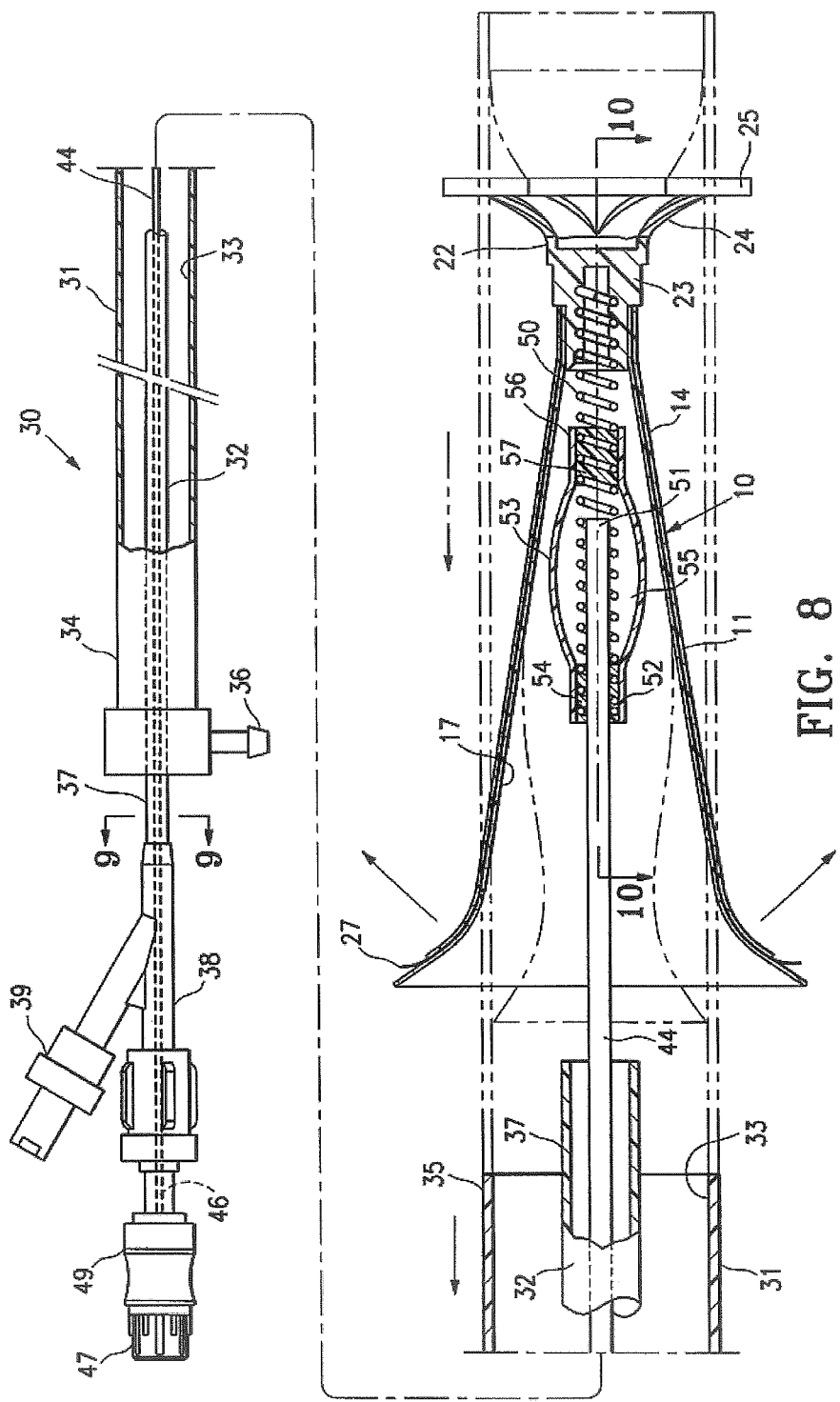
FIG. 8 is a schematic elevational view, partially in section, of a delivery system with the expandable device shown in FIGS. 1 and 2 mounted thereon.

The hub 12 shown in FIGS. 4 and 5 is connected to a non-traumatic support component or foot 22. The support component 22 has a stem 23, a plurality of petals or pods 24 extending radially away from the center line axis and the ends of the petals 24 are secured to struts 25 which extend between adjacent petals. A plane of material (not shown) may extend between adjacent petals 24 in a web-like fashion to provide further support in addition to or in lieu of the struts 25. The inner diameter of the stem 23 is threaded to secure the expandable device 10 to a delivery catheter as shown in FIGS. 8-10.

As shown in FIG. 5, the second ends 15 of the ribs 14 are secured within the hub 12 and, as shown in FIG. 6, a transversely disposed connector bar 26 is secured within the hub, which is configured to secure the hub 12 to the non-traumatic support component 22.

Figure 2:
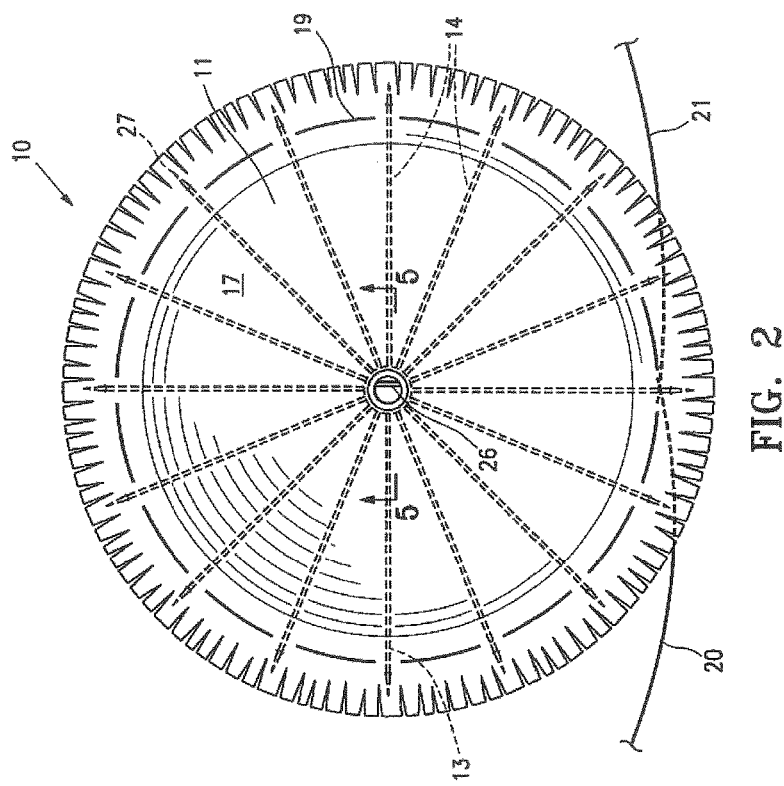
FIG. 2 is a plan view of the expandable device shown in FIG. 1 illustrating the upper surface of the device.
Figure 3:
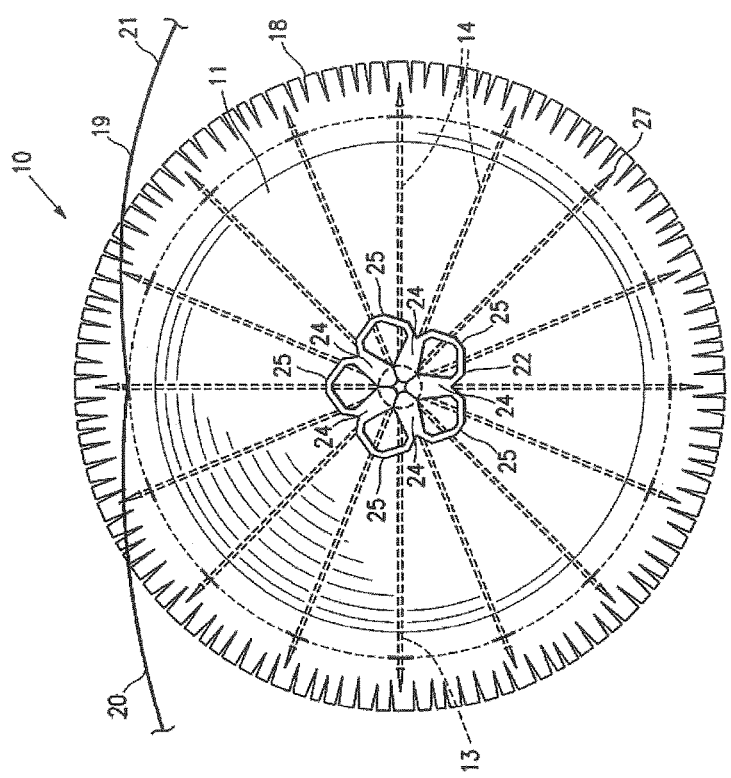
FIG. 3 is a bottom view of the expandable device shown in FIG. 1.

As illustrated in FIGS. 5 and 6, the connector bar 26 of the hub 12 allows the expandable device 10 to be secured to the non-traumatic support component 22 and to be released from the delivery system within the patient's heart chamber. The second ends 15 of the reinforcing ribs 14 are secured within the hub 12 in a suitable manner or they may be secured to the surface defining the inner lumen or they may be disposed within channels or bores in the wall of the hub 12. The second end of the ribs 14 are preshaped so that when the ribs are not constrained, other than by the membrane 11 secured thereto (as shown in FIGS. 1 and 2), the first free ends 16 thereof expand to a desired angular displacement away from the centerline axis which, in some embodiments, is about 20° to about 90°. In one embodiment, the desired angular displacement away from the centerline axis is about 50° to about 80°. The unconstrained diameter of the expandable device 10 should be greater than the diameter of the heart chamber at the deployed location of the expandable device so that an outward force is applied to the wall of the heart chamber by the partially expanded ribs 14 during systole and diastole so that the resilient frame 13 augments the heart wall movement.

FIG. 7 illustrates the curved first free ends 16 of ribs 14 which are provided with sharp tip or anchor elements 27 configured to engage and penetrate into the wall of the heart chamber and hold the expandable device 10 in a deployed position within the patient's heart chamber so as to partition the ventricular chamber into a productive portion and a non-productive portion.

In some embodiments, the expandable device further includes a suture 19 extending around the periphery of the membrane 11 on the pressure side thereof to apply pressure to the pressure side of the flexible material of the membrane to effectively seal the periphery of the membrane against the wall of the ventricular chamber. The ends 20 and 21 of the suture 19 are shown extending away from the expandable device in FIGS. 2 and 3. The ends 20 and 21 may be left unattached or may be secured together, for example by a suitable adhesive or the membrane 11 itself. In other embodiments, the suture is removed from the implant after the device is expanded in the ventricle, as described in further detail elsewhere herein.

FIGS. 8-10 illustrate a delivery system 30 for delivering the expandable device 10 shown in FIGS. 1 and 2 into a patient's heart chamber and deploying the expandable device to partition the heart chamber as shown in FIGS. 11A-11E. The delivery system 30 includes a guide catheter 31 and a delivery catheter 32.

As shown in FIG. 8, the guide catheter 31 has an inner lumen 33 extending between the proximal end 34 and distal end 35. A hemostatic valve may be provided at the proximal end 34 of the guide catheter 31 to seal about the outer shaft 37 of the delivery catheter 32. A flush port 36 on the proximal end 34 of guide catheter 31 is in fluid communication with the inner lumen 33.

The delivery catheter includes a proximal end, a distal end, and a tubular shaft therebetween. The tubular shaft includes an outer shaft 37 and an inner shaft 41 disposed within the outer shaft 37. The outer shaft 37 includes an adapter 38 on the proximal end thereof having a proximal injection port 39, which is in fluid communication with the interior of the outer shaft 37. As shown in more detail in FIG. 9, the inner shaft 41 is disposed within the interior of the outer shaft 37 and is secured to the inner surface of the outer shaft 37 by webs 43 which extend along a substantial length of the inner shaft. The injection port 39 is in fluid communication with the passageways 42 between the inner and outer shafts 41 and 37, respectively, and defined in part by the webs 43.

In some embodiments, the delivery catheter includes a torque shaft 44. The torque shaft, which, for example, is formed of hypotubing (e.g., formed of stainless steel or superelastic NiTi), is disposed within the inner lumen 45 of the inner shaft 41 and has a proximal end 46 secured within the adapter 38. An expansion member inflation port 47 is in fluid communication with the inner lumen 48 of the torque shaft 44. Torque shaft 44 is rotatably disposed within the inner lumen 45 of the inner shaft 41 and is secured to rotating knob 49. A coupling element 50, for example a helical coil screw, is secured to the distal end 51 of the torque shaft 44 and rotation of the torque knob 49 on the proximal end 46 of the torque shaft 44 rotates the coupling element 50, for example a balloon, coupled to the expandable device 10 to facilitate deployment of the expandable device 10. The proximal end 52 of inflatable expansion member 53 is sealingly secured by adhesive 54 about the torque shaft 44 proximal to the distal end 51 of the torque shaft. The expansion member 53 has an interior 55 in fluid communication with the inner lumen 48 of the torque shaft 44. Inflation fluid may be delivered to the expansion member interior 55 through port 47 which is in fluid communication with the inner lumen 48 of the torque shaft 44. The distal end 56 of the expansion member 53 is sealingly secured by adhesive 57 to the coupling element 50. The proximal 52 and distal ends 56 of the expansion member 53 are blocked by the adhesive masses 54 and 57 to prevent the loss of inflation fluid delivered to the interior 55 of the expansion member 53. Delivery of inflation fluid through a fluid discharge port 58 in the distal end 51 of the torque shaft 44 inflates the expansion member 53 which in turn applies pressure to the proximal surface of the expandable device 10 to facilitate securing the expandable device 10 to the wall 59 of heart chamber 60 as shown in FIGS. 11A-11F.

Figure 11A:
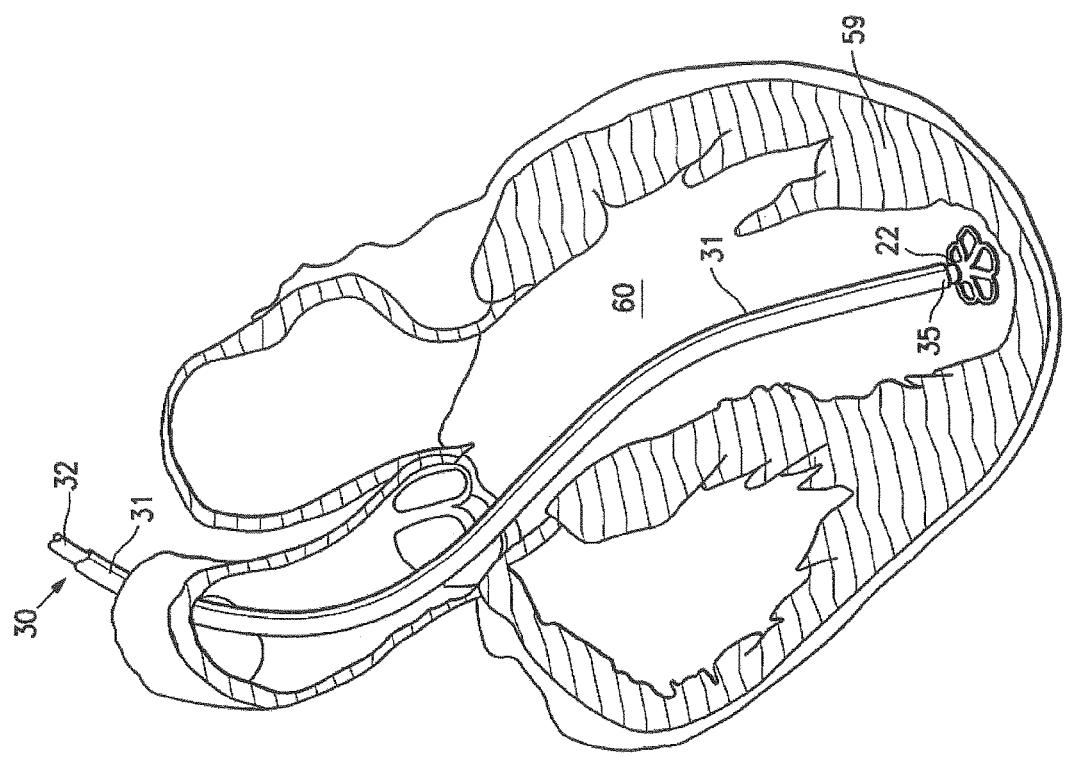
FIGS. 11A-11F are schematic sequential views of a patient's left ventricular chamber illustrating the deployment of the expandable device shown in FIGS. 1 and 2 with the delivery system shown in FIG. 8 to partition a patient's heart chamber (left ventricle) into a primary productive portion and a secondary, non-productive portion.

As shown in FIG. 11A, the expandable device 10 is delivered through a delivery system 30 which includes a guide catheter 31 and a delivery catheter 32. The expandable device 10 is collapsed in a first, delivery configuration which has small enough transverse dimensions to be slidably advanced through the inner lumen 33 of the guide catheter 31. In some embodiments, the guide catheter 31 has been previously percutaneously introduced and advanced through the patient's vasculature, such as the femoral artery, in a conventional manner to the desired heart chamber 60. The delivery catheter 32 with the expandable device 10 attached is advanced through the inner lumen 33 of the guide catheter 31 until the expandable device 10 is ready for deployment from the distal end of the guide catheter 31 into the patient's heart chamber 60 to be partitioned.

Figure 11B:
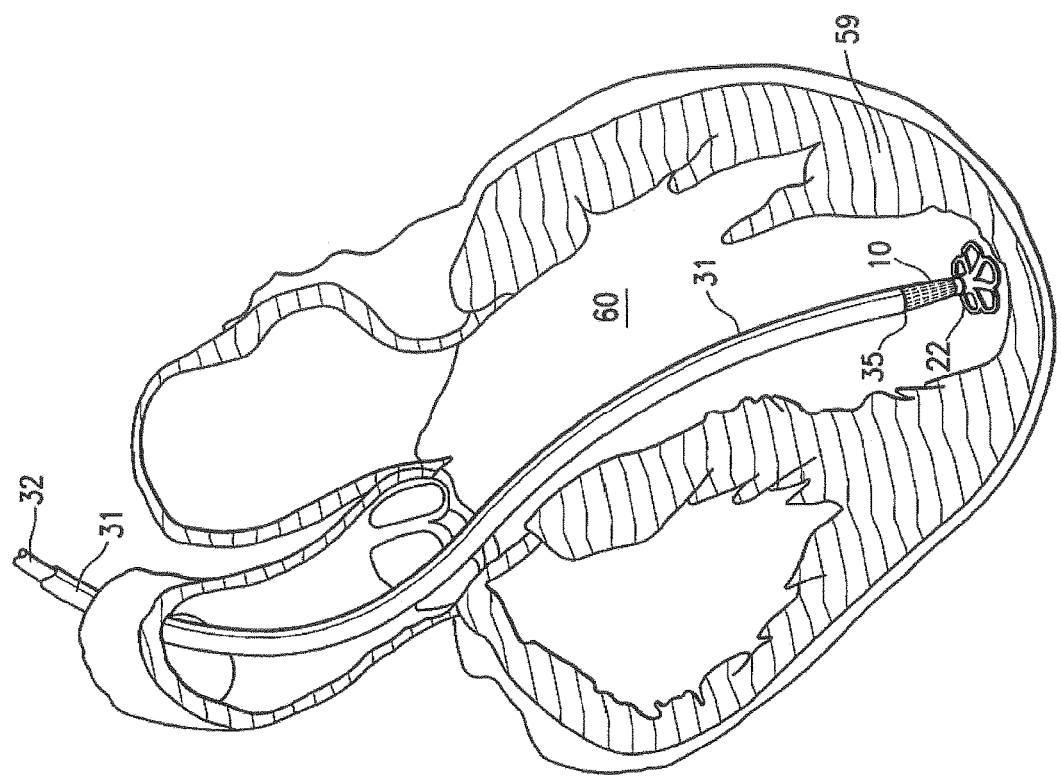
Figure 11C:
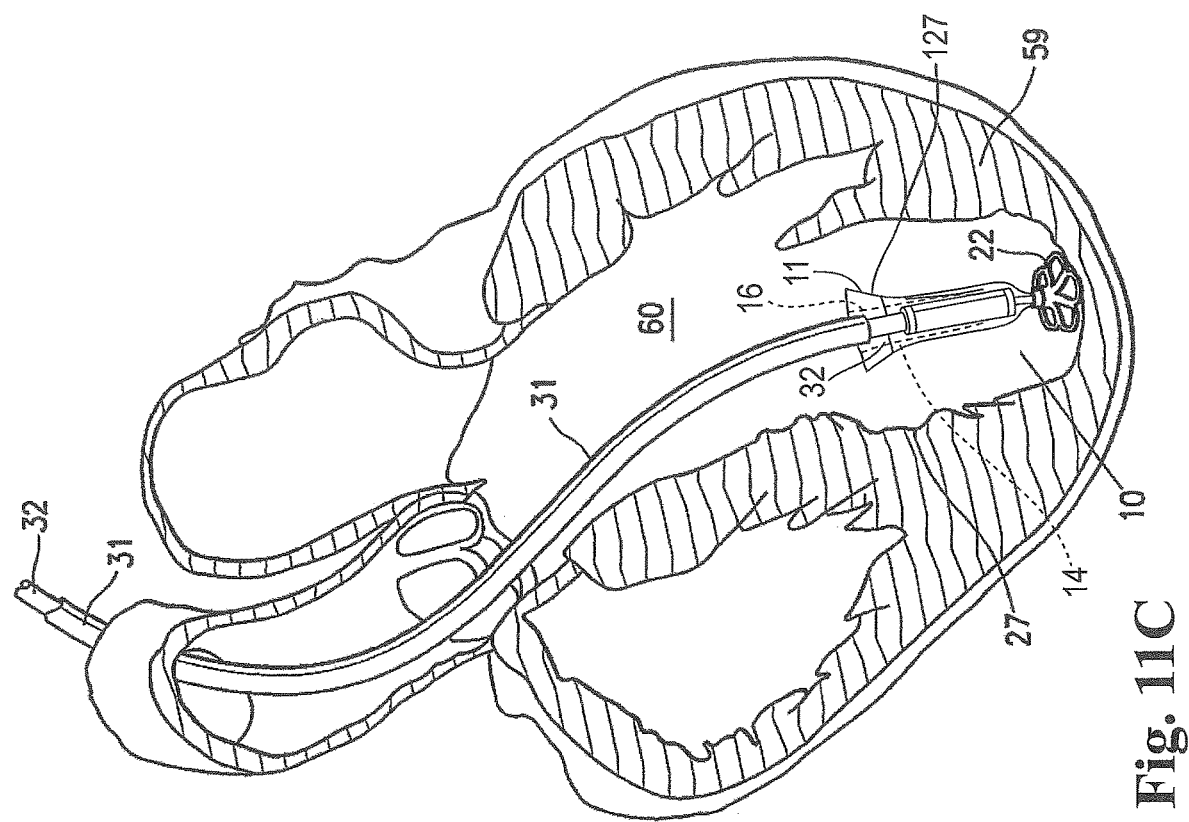

As shown in FIG. 11B, the expandable device 10 mounted on the coupling element 50 of the delivery catheter is urged further out of the inner lumen 33 of the guide catheter 32 until the support component 22 touches or engages the heart wall 59. The guide catheter 31 is withdrawn while the delivery catheter 32 is held in place until the first free ends 16 of the ribs 14 exit the distal end 35 of the guide catheter. As shown in FIG. 11C, the first free ends 16 of ribs 14 remain in an unexpanded configuration due to tension in the suture extending around the perimeter, first region, or anchor region of the expandable device.

Figure 11D:
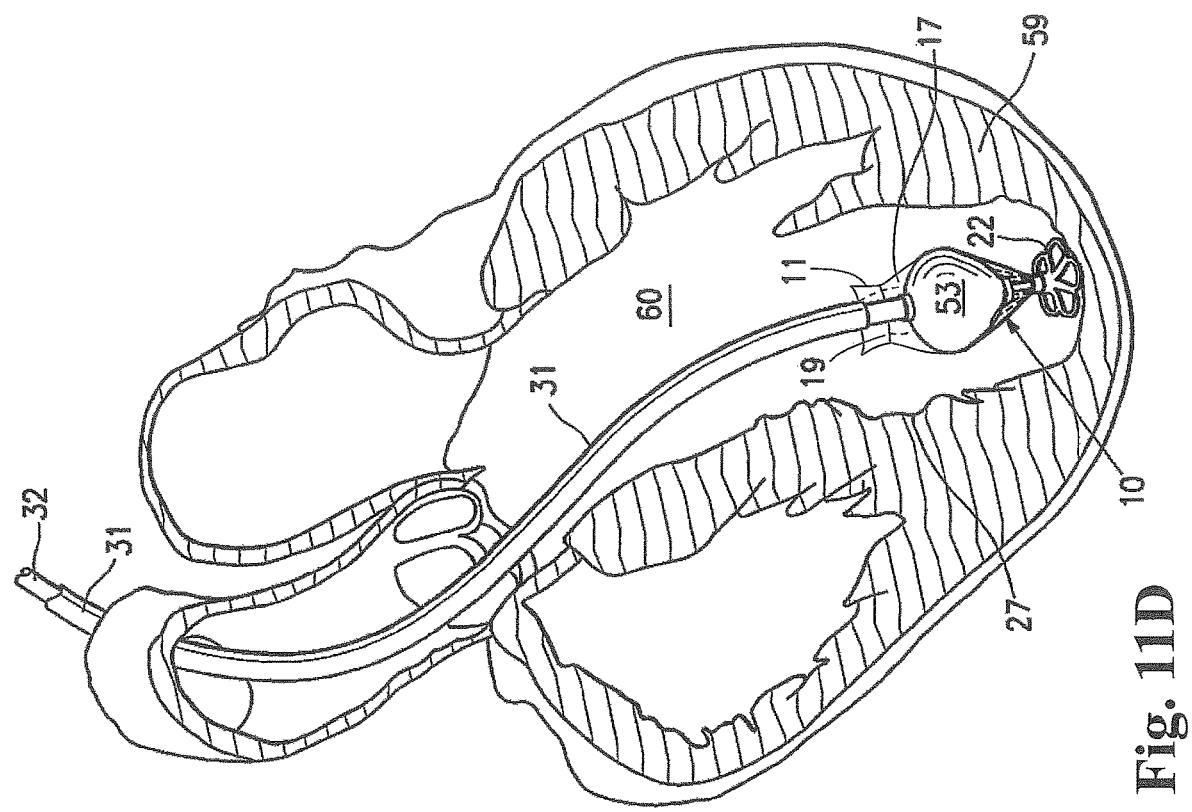

With the expandable device 10 positioned within the heart chamber 60, inflation fluid is introduced through the inflation port 58 in the distal end 51 of torque shaft 44 where it is directed into the expansion member interior 54 to inflate the expansion member 53. The inflated expansion member 53 presses against the pressure receiving surface 17 of the membrane 11 of the expandable device 10 to expand the second region or foot region of the expandable device while the first region or perimeter of the expandable device remains contracted, as shown in FIG. 11D.

Figure 11E:
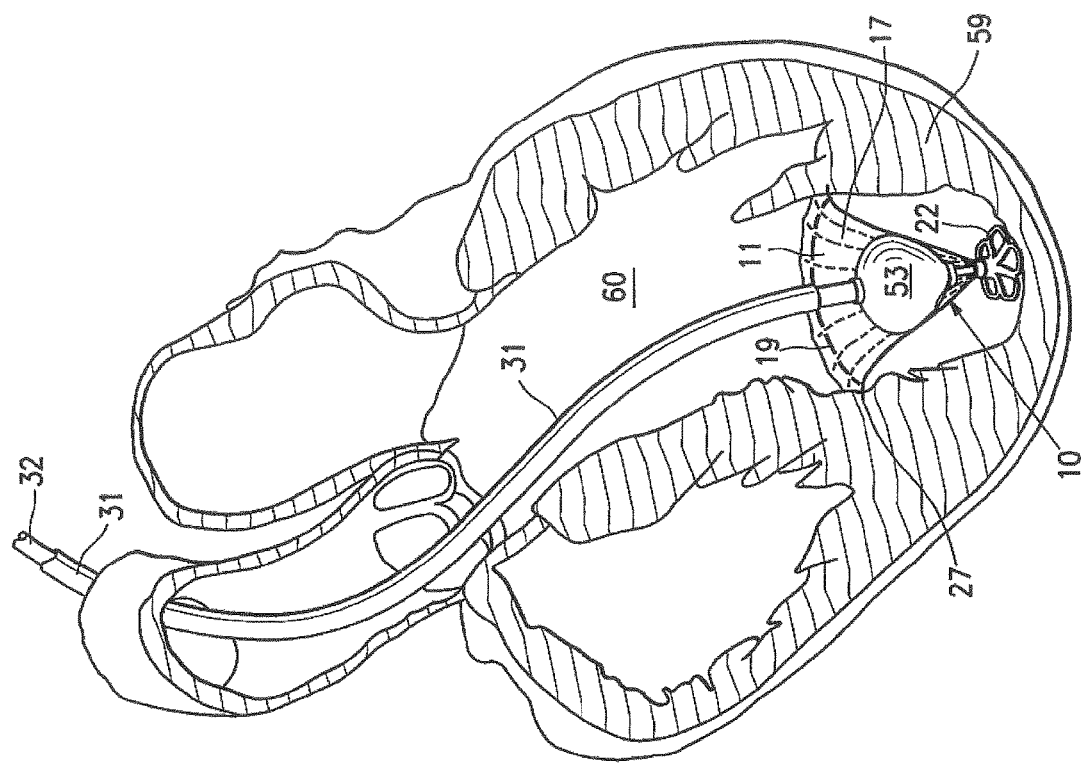

With the expandable device positioned in the heart chamber and the first region of the expandable device expanded, the tension in the suture around the perimeter or in the second region of the expandable device is relieved, so that each of the first free ends of the ribs expand outwardly to press the sharp proximal tips or anchors of the first free ends of the ribs against and into the tissue lining the heart wall, as shown in FIG. 11E. In some such embodiments, the tension in the suture is relieved by releasing the first end and the second end of the suture.

Figure 11F:
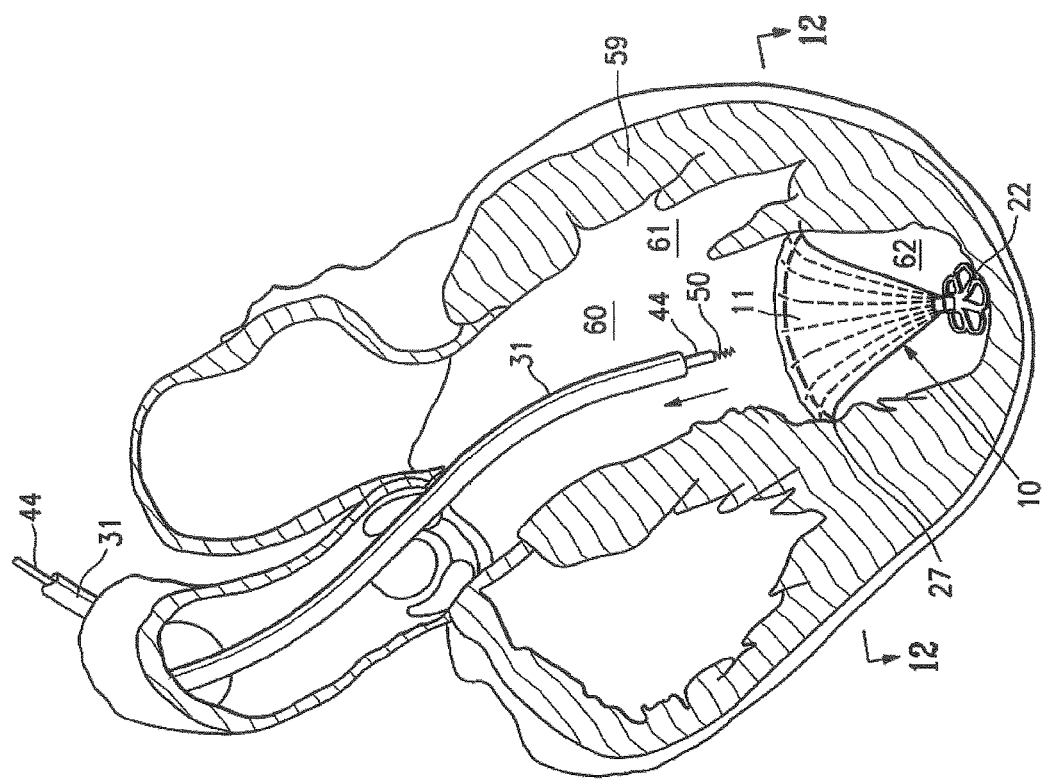

With the expandable device 10 positioned within the heart chamber 60, the knob 49 on the torque shaft 44, as shown in FIG. 8, is rotated counter-clockwise to disengage the coupling element 50 of the delivery catheter 32 from the stem 23 secured within hub 12. The counter-clockwise rotation of the torque shaft 44 rotates the coupling element 50 which rides on the connector bar 26 secured within the hub 12. Once the coupling element 50 disengages the connector bar 26, the delivery system 30, including the guide catheter 31 and the delivery catheter 32, may then be removed from the patient, as shown in FIG. 11F. The deployment of the expandable device 10 in the patient's heart chamber 60, as shown in FIG. 11F, divides the chamber into a main productive or operational portion 61 and a secondary, substantially non-productive portion 62. The operational portion 61 is smaller than the original heart chamber 60 and provides for an improved ejection fraction and an improvement in blood flow.

Figure 12:
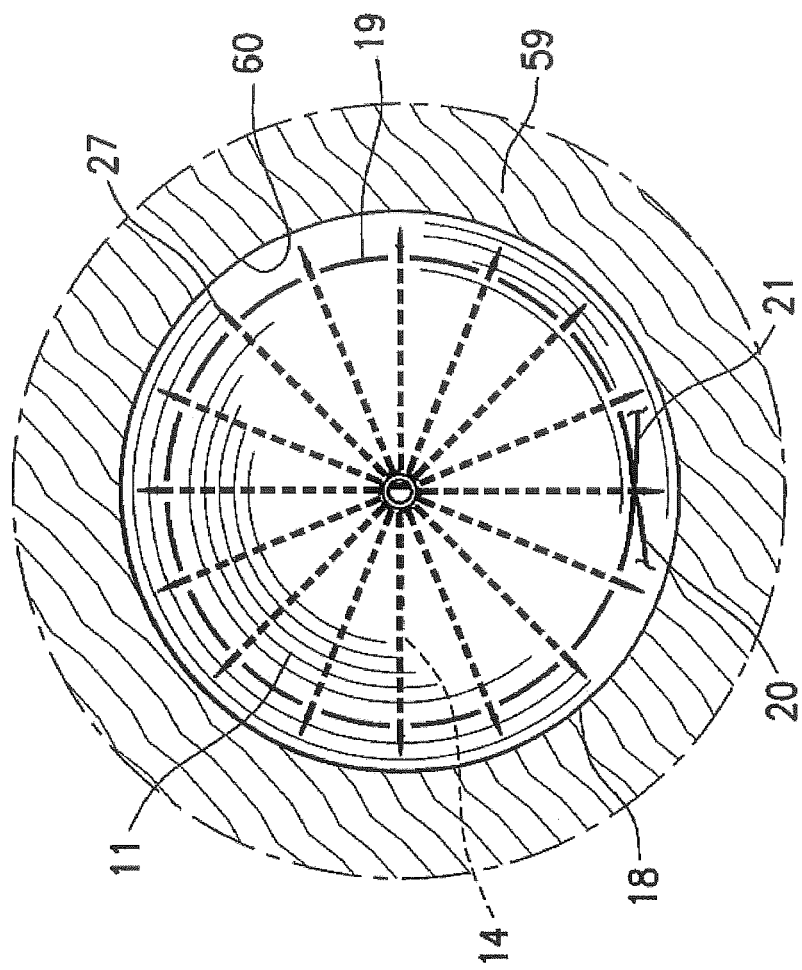
FIG. 12 is a schematic plan view of the deployed device shown in FIG. 11E within a patient's heart chamber.

FIG. 12 is a top view of the deployed expandable device shown in FIG. 11F schematically illustrating the sealed or substantially sealed periphery of the membrane 11 against the ventricular wall. The expandable device 10 may be conveniently formed by the method described in U.S. application Ser. No. 10/913,608, filed Aug. 5, 2004, which is incorporated herein by reference.

Figure 13A:
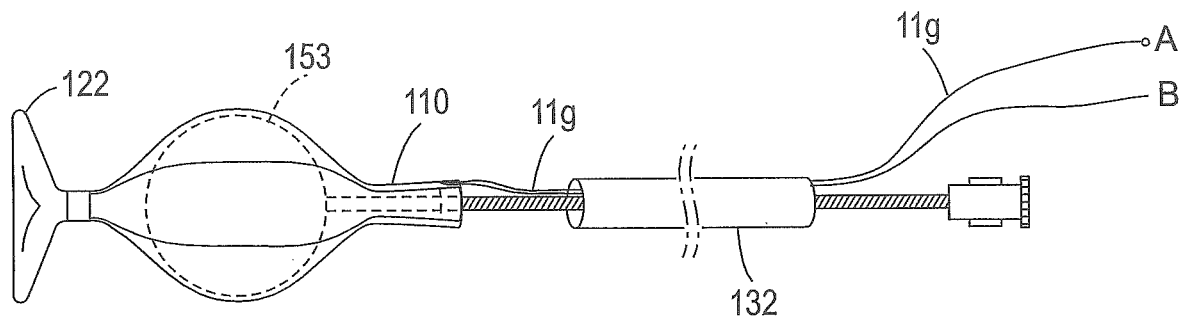
FIGS. 13A-13C are schematic sequential views of a system for positioning or retrieving an expandable device.
Figure 13B:
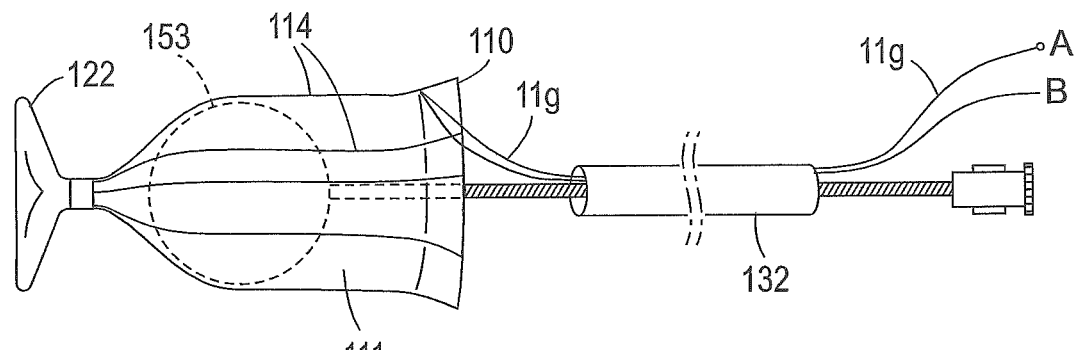
Figure 13C:
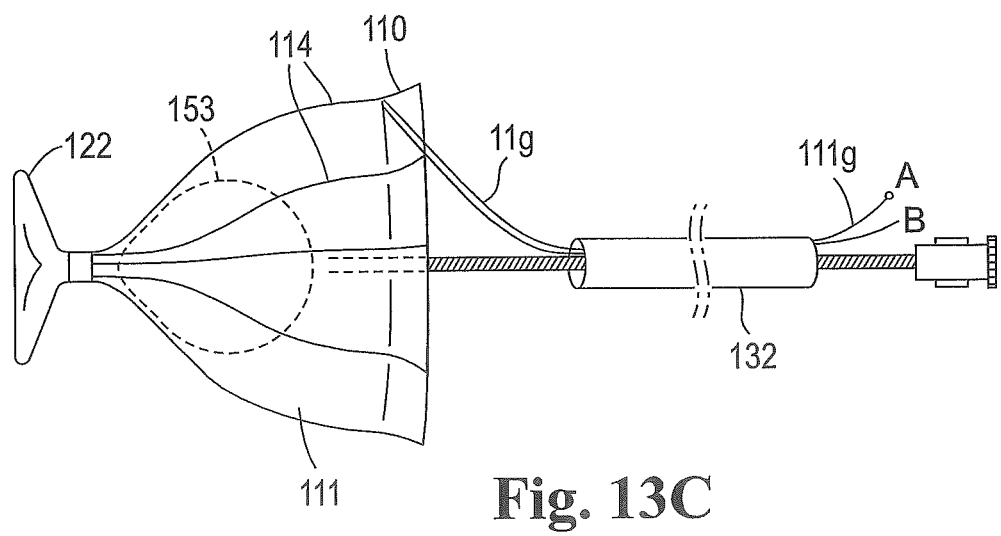

In some embodiments, as shown in FIGS. 13A-14B, a system for positioning an expandable device 110 further includes means for manipulating one or both ends of a suture 119 that extends around a perimeter region of the expandable device 110. In some embodiments, as shown in FIGS. 13A-13C, the means includes both ends of the suture 119 extending from a proximal opening of the tubular shaft of the delivery catheter 132. FIGS. 13A-13C illustrate controlled expansion or retrieval of an expandable device 110 by manipulating ends A and B of suture 119. As shown in FIGS. 13A-13C, the expandable device 110 is secured to the delivery catheter 132 and the expandable device 110 is shown in a partially expanded configuration. In the partially expanded configuration, the expansion member 110 is inflated via balloon 153 and suture ends A and B are tensioned and extending out of the proximal end of the delivery catheter 132, so that a second region of the expandable device proximal the foot 122 is expanded while a first region or perimeter region of the expandable device is contracted or unexpanded. As shown in FIG. 13B, the tension in the suture 119 is at least partially relieved (for deployment) by allowing suture ends A and B to move towards or recoil towards the proximal end of the delivery catheter from which the suture ends extend. The first region or perimeter region of the expandable device, as shown in FIG. 13B, is in a partially expanded configuration. As shown in FIG. 13C, the tension in the suture 119 is fully relieved enabling expansion and deployment of the expandable device, so that a perimeter of the membrane 111 on ribs 114 expands with an outward expansive force and contacts an interior wall portion of the ventricle.

Figure 14A:
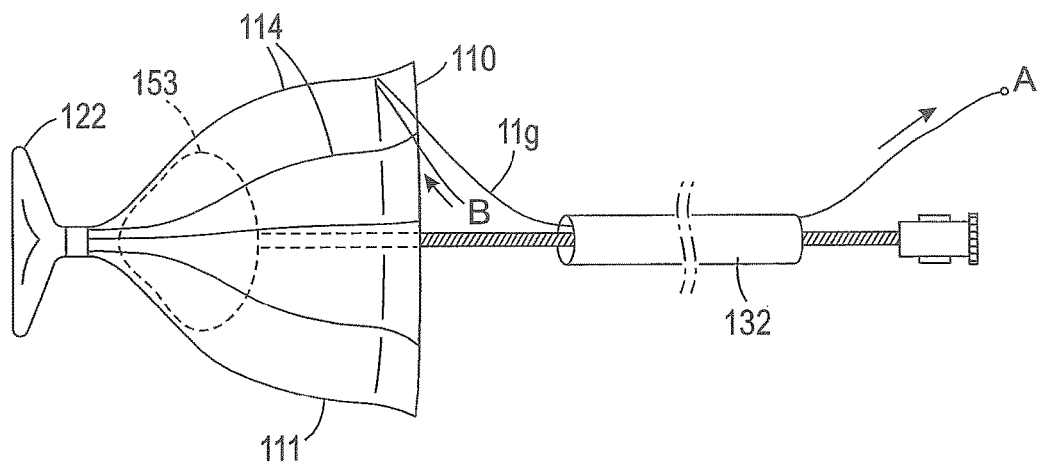
FIGS. 14A-14B are schematic sequential views of a system for positioning or retrieving an expandable device.
Figure 14B:
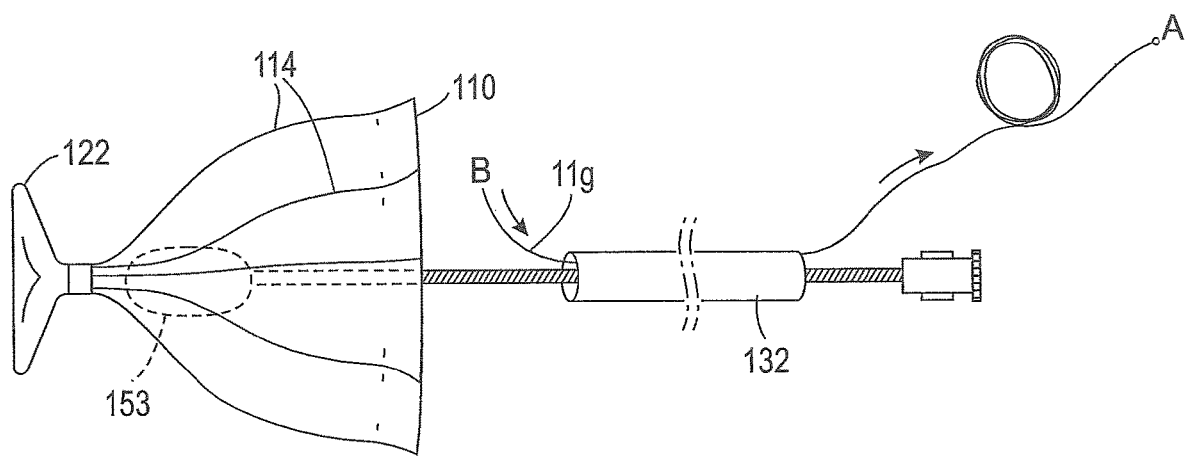

As shown in FIGS. 14A-14B, the expandable device is released by pulling one end of the suture 119 until the suture is removed from the perimeter of the membrane 111. Suture end A is tensioned and pulled away from the proximal end of the delivery catheter from which it extends. Suture end B travels around the perimeter of the membrane as suture end A is pulled, as shown in FIG. 14B, until the entire length of the suture is released from the perimeter of the membrane and the membrane is fully expanded.

In some embodiments, the first region or perimeter region of the expandable device 110 may be collapsed by tensioning one or both ends of the suture, and the expansion member may be collapsed or deflated, so that the expandable device may be repositioned or retrieved from the heart chamber.

In some embodiments, as shown in FIG. 13A, the expandable device is preloaded onto the torque shaft of the delivery catheter with one or both ends of the suture 119 extending through the tubular shaft (e.g., inner or outer shaft) of the delivery catheter and out a proximal end of the delivery catheter. In some embodiments, one or both ends of the suture will require threading through the tubular shaft (e.g., inner or outer shaft) of the delivery catheter to prepare the expandable device for delivery.

In some embodiments, there is substantial friction between the suture 119 and the delivery catheter when the suture ends are manipulated from a proximal end of the delivery catheter. In some such embodiments, the implant may collapse during release of the suture as a result of the friction. To reduce friction, the means may include extending one end of the suture from a proximal opening of the tubular shaft of the delivery catheter, so that there is a shorter length of suture in contact with the delivery catheter, as shown in FIG. 15.

Figure 15:
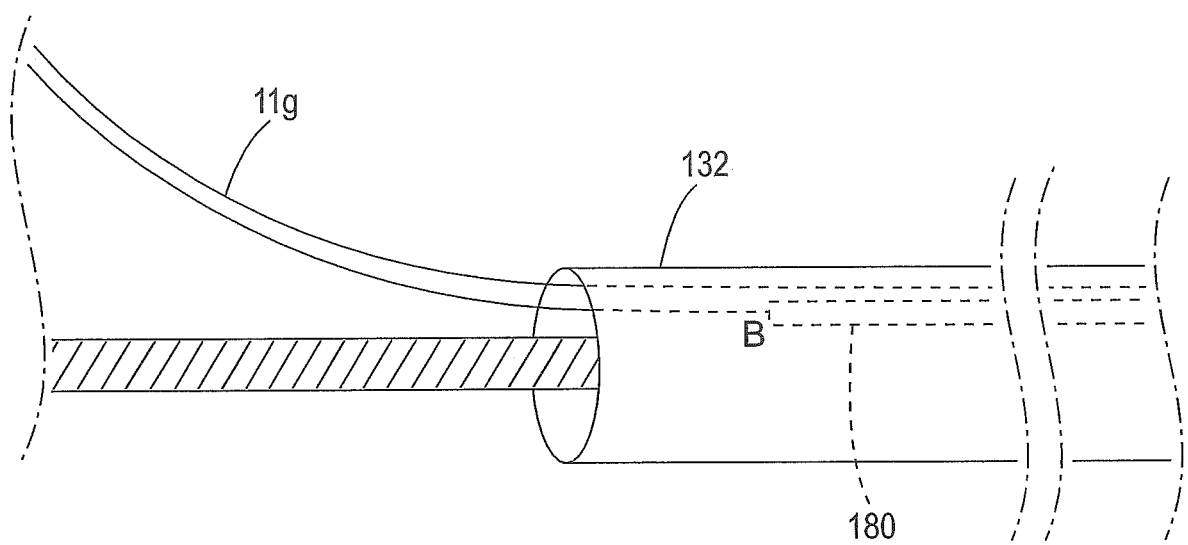
FIG. 15 is a schematic view of a means of a delivery catheter for positioning or retrieving an expandable device.

In some embodiments, as shown in FIG. 15, the means includes a hypotube 180 on the distal end of the delivery catheter. The hypotube 180 includes a slot for receiving and manipulating one end of the suture, such that twisting or turning the hypotube, and therefore the slot, tensions or relieves tension in the suture and contracts or expands the expandable device, respectively.

In some embodiments, the means includes a clamp or jaws on the distal end of the delivery catheter. The clamp or jaws are configured for securing and manipulating at least one end of the suture to tension the suture, release tension in the suture, or completely remove the suture from the expandable device.

In some embodiments, as shown in FIGS. 16A and 16B, a system for positioning an expandable device further includes a diagnostic instrument 180. The diagnostic instrument functions to measure one or more hemodynamics of the heart before, during, and/or after device placement in the ventricle of the heart. The diagnostic instrument measures one or more of blood pressure (i.e., systolic and/or diastolic), mean arterial pressure, cardiac index, cardiac output, central venous pressure (i.e., right atrial pressure), pulmonary arterial pressure, pulmonary capillary wedge pressure, pulmonary vascular resistance, right ventricular pressure, stroke index, stroke volume, systemic vascular resistance, blood flow vectors, and/or any other hemodynamic measurement.

Considering FIG. 16A, for example, one diagnostic instrument 182 has a metal outer casing 184 with a plastic nose 186. Piezoelectric crystal 188 is housed inside the plastic nose 186. Electrodes 190 apply an alternating potential difference. The device also includes an acoustic insulator 192, a power cable 194 to supply power, and a backing block 196. Many other diagnostic instruments may be employed.

In some embodiments, the diagnostic instrument measures preload (i.e., amount of myocardial fiber stretch at the end of diastole). For example, left atrial filling pressure or pulmonary artery wedge pressure is used to assess left ventricular preload, and right atrial pressure is used to assess right ventricular preload. In some embodiments, the diagnostic instrument measures afterload (i.e., tension developed by the myocardium during ventricular systolic ejection). Afterload is dependent on a number of factors, including volume and mass of blood ejected, the size and wall thickness of the ventricles, and the impedance of the vasculature. For example, systemic vascular resistance (SVR) for the left ventricle and pulmonary vascular pressure (PVR) for the right ventricle is a measure of afterload.

In some embodiments, the diagnostic instrument includes a thermocouple wire coupled to the delivery system, for example the outer shaft of the guide catheter, the lumen of the outer shaft of the delivery catheter, the lumen of the inner shaft of the delivery catheter, coupling element, expansion member, or any other component of the delivery catheter. In one non-limiting example, the delivery system is configured to measure cardiac output, similar to a Swan-Ganz Catheter.

In some embodiments, the diagnostic instrument includes an ultrasound transducer configured for monitoring one or more hemodynamics in the ventricle of the patient. In some embodiments, the ultrasound transducer can be mounted on a catheter or guidewire or guide sheath, for example. In other embodiments, the ultrasound transducer can be mounted on an external device for noninvasive diagnostics. In some embodiments, the diagnostic instrument includes an echocardiogram, an electrocardiogram, a pulse oximeter, a peripheral arterial line, a peak endocardial acceleration sensor, a transvalvular impedance sensor, a closed loop stimulation, or any other sensor or instrument. In some embodiments, the diagnostic instrument is configured to perform Vector Flow Mapping (VFM), for example using Color Doppler velocity data to derive velocity fields and display them on a 2D image to illustrate cardiovascular blood flow distribution in an observation plane.

In some embodiments, the system further includes a display for displaying one or more images of the expandable device in a ventricle of a patient. In some embodiments, the display includes a Thin Film Transistor liquid crystal display (LCD), in-place switching LCD, resistive touchscreen LCD, capacitive touchscreen LCD, organic light emitting diode (LED), Active-Matrix organic LED (AMOLED), Super AMOLED, Retina display, Haptic/Tactile touchscreen, and/or Gorilla Glass. The display may include user input controls, which enable a user to interact with the display and/or system. The display may include buttons, sliders, toggle buttons, toggle switches, switches, dropdown menus, combo boxes, text input fields, check boxes, radio buttons, picker controls, segmented controls, steppers, and/or any other type of control. In some embodiments, the user may use different tactile or haptic lengths or pressures to navigate on the display. For example, a user may use a short press, long press, light press, or forceful press to navigate on the display.

In some embodiments, the image displayed on the display may include a 2-dimensional image or a 3-dimensional image. In some embodiments, the image includes a B-mode image, a color Doppler image, a color power Doppler image, a directional color power Doppler mode image, or any other type of image.

In some embodiments, to assist in properly locating the device during advancement and placement thereof into a patient's heart chamber, a portion of, for example the distal extremity of, one or more of the ribs 14, the hub 12, and/or the foot may be provided with markers at desirable locations that provide enhanced visualization by eye, by ultrasound, by X-ray, or other imaging or visualization means. Radiopaque markers may be made with, for example, stainless steel, platinum, gold, iridium, tantalum, tungsten, silver, rhodium, nickel, bismuth, other radiopaque metals, alloys and oxides of these metals.

In some embodiments, the system further includes a processor for executing one or more sets of instructions of the system. For example, the processor may monitor velocity measurements in the heart chamber, derive one or more velocity fields from the velocity measurements, and display the one or more velocity fields on a two-dimensional image. In some embodiments, the processor performs the method of FIG. 19, described elsewhere herein.

In some embodiments, the diagnostic instrument can be integrated into the delivery catheter, a guide sheath, or other component of the delivery system. In some embodiments, the diagnostic instrument can be an independent device that is inserted alongside the delivery catheter and/or after the delivery catheter is withdrawn. In some embodiments, the diagnostic instrument can be an external device used for noninvasive transcutaneous measurements, such as transcutaneous Doppler ultrasound for determining blood flow measurements.

Methods

As shown in FIG. 17, a method for controllably deploying an expandable device in a ventricle of a patient includes positioning the expandable device in the ventricle of the patient S100; deploying an expansion member, near a distal end of a delivery catheter, coupled to the expandable device to apply pressure to a second region of a support frame of the expandable device to expand the second region of the support frame S110; and controllably releasing a first end or a second end of a suture coupled to a first region of the expandable device to secure the first region of the expandable device in the ventricle of the patient S120. The method functions to increase an outward expansive force of the support frame by controllably releasing one or both ends of the suture coupled to or threaded through the expandable device.

In some embodiments, positioning the expandable device in the ventricle of the patient S100 includes delivering and positioning a guide catheter in a ventricle of a patient and advancing a delivery catheter, coupled to the expandable device, through the guide catheter into the ventricle of the patient. In some embodiments, positioning the expandable device in the ventricle includes visualizing the expandable device and/or delivery catheter during positioning using, for example a diagnostic instrument, one or more contrast dyes, or any other technique or instrument.

In some embodiments, deploying the expansion member S110 includes delivering a liquid, for example through the expansion member inflation port on the torque shaft of the delivery catheter, to inflate the expansion member. Further, in some embodiments, deploying the expansion member includes moving the expandable device from a first, unexpanded configuration to a second partially expanded configuration. The second partially expanded configuration is characterized by an expanded second or foot region of the expandable device and a contracted or unexpanded second or anchor region of the expandable device, so that the expandable device resembles an onion or bulb.

In some embodiments, controllably releasing a first end or a second end of a suture coupled to a first region of the expandable device to secure the first region of the expandable device in the ventricle of the patient S120 includes manipulating one or more means or mechanisms on the delivery catheter to controllably release the first end and/or second end of the suture. In some embodiments, S110 is performed substantially simultaneously as S120. In some embodiments, S120 is performed before S110. In some embodiments, S120 is performed after S110.

In some embodiments, the method shown in FIG. 17 is performed in reverse to reposition the expandable device in the ventricle or retrieve the expandable device from the ventricle. As shown in FIG. 18, a method for controllably repositioning or retrieving an expandable device from a ventricle of a patient includes controllably tensioning a first end or a second end of a suture coupled to a first or anchor region of the expandable device to contract the first region of the expandable device S200; deflating an expansion member, near a distal end of a delivery catheter, coupled to the expandable device to contract a second region of a support frame of the expandable device S210; and repositioning or retrieving the expandable device from the ventricle of the patient S220. The method functions to controllably contract the expandable device to facilitate repositioning or retrieval of the expandable device.

In some embodiments, controllably tensioning a first end or a second end of a suture coupled to a first or anchor region of the expandable device to contract the first region of the expandable device S200 includes manipulating one or more means or mechanisms on the delivery catheter to controllably tension the first end and/or second end of the suture.

In some embodiments, deflating the expansion member S210 includes removing a liquid from the interior of the expansion member, for example through the expansion member inflation port on the torque shaft of the delivery catheter. Further, in some embodiments, deflating the expansion member includes moving the expandable device from a third, fully expanded configuration to a second, partially expanded configuration to a first, unexpanded configuration. The third, fully expanded configuration is characterized by a fully expanded first and second region of the expandable device, so that the expandable device forms a trumpet, umbrella, hemispherical shape, or otherwise cupped pressure-receiving surface. The second partially expanded configuration is characterized by an expanded second or foot region of the expandable device and a contracted or unexpanded first or anchor region of the expandable device, so that the expandable device resembles an onion or bulb. In some embodiments, S200 is performed substantially simultaneously as S210. In some embodiments, S200 is performed before S210. In some embodiments, S200 is performed after S210.

In some embodiments, repositioning or retrieving the expandable device from the ventricle of the patient S220 includes visualizing the expandable device and/or delivery catheter during repositioning and/or retrieval using, for example the diagnostic instrument, one or more contrast dyes, or any other technique or instrument.

Figure 19:
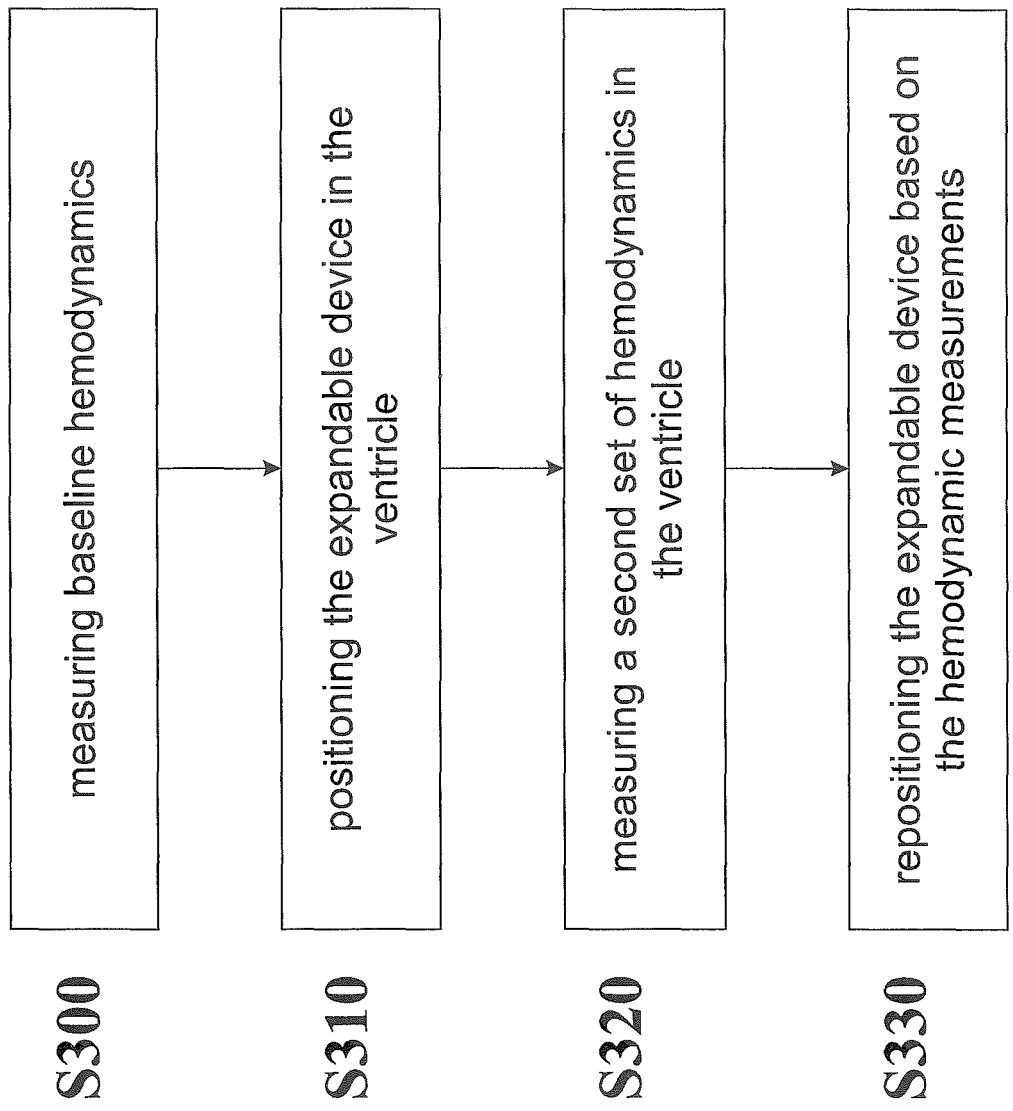
FIG. 19 is a flow chart illustrating a method of monitoring blood flow dynamics in a ventricle during positioning of an expandable device in the ventricle.

In some embodiments, determining where to position the expandable device and/or whether to reposition or retrieve the expandable device includes determining how the position of the expandable device impacts the hemodynamics of the ventricle. In some embodiments, as shown in FIG. 19, a method of monitoring blood flow dynamics in a ventricle during positioning of an expandable device in the ventricle includes measuring baseline hemodynamics S300; positioning the expandable device in the ventricle S310; measuring a second set of hemodynamics in the ventricle S320; and repositioning the expandable device based on the hemodynamic measurements S330.

In some embodiments, measuring baseline hemodynamics S300 includes measuring hemodynamics of the heart before device placement in the ventricle and/or device repositioning in the ventricle. In some embodiments, measuring baseline hemodynamics S300 includes measuring blood pressure (i.e., systolic and/or diastolic), mean arterial pressure, cardiac index, cardiac output, central venous pressure (i.e., right atrial pressure), pulmonary arterial pressure, pulmonary capillary wedge pressure, pulmonary vascular resistance, right ventricular pressure, stroke index, stroke volume, systemic vascular resistance, and/or one or more blood flow vectors. In some embodiments, the baseline hemodynamics may represent unfavorable hemodynamics for heart or ventricle function.

In some embodiments, measuring a second set of hemodynamics in the ventricle S310 includes measuring the second set of hemodynamics in the ventricle after device placement in the ventricle or after device retrieval or removal from the ventricle. In some embodiments, measuring includes non-invasive measurement with a diagnostic instrument, for example ultrasound; in some embodiments, measuring includes an invasive measurement with a diagnostic instrument, for example a catheter or electric lead. In some embodiments, measuring baseline or a second set of hemodynamics includes using a diagnostic instrument coupled to the delivery system, for example a thermocouple.

In some embodiments, repositioning the expandable device based on the hemodynamic measurements S330 includes retrieving the expandable device or removing the expandable device from the ventricle. In some embodiments, the device is repositioned or removed because the second set of hemodynamics are more or less favorable than the baseline hemodynamics. In some embodiments, the device is repositioned or removed because the second set of hemodynamics are above or below a threshold.

In some embodiments, as shown in FIGS. 20A-20B, repositioning the expandable device functions to attempt to restore a more normal flow surface to the ventricle which may result in a more normal flow pattern. In some embodiments, repositioning the expandable device includes aligning the expandable device with the left ventricular outflow path, which is the portion of the left ventricle 3612 that extends between the apex 3616 or apical portion of the left ventricle and the aortic valve 3614, such that the membrane of the device receives flow from the left atrium exiting the mitral valve 3613 and redirects it towards the aortic valve 3614 to exit the left ventricle, thereby restoring a more normal flow pattern within the ventricle. In some embodiments, the method includes aligning the expandable device with the aortic valve such that at least a portion of the pressure or flow receiving surface of the membrane generally faces the aortic valve. In some embodiments, the method includes aligning a central axis extending through the hub of the device 3630 with the left ventricular outflow tract and/or aortic valve. In some embodiments, repositioning the expandable device includes eliminating vortices and/or blood swirling in the ventricle and/or redirecting blood flow out of the ventricle As used in the description and claims, the singular form "a", "an" and "the" include both singular and plural references unless the context clearly dictates otherwise. For example, the term "strut" may include, and is contemplated to include, a plurality of struts. At times, the claims and disclosure may include terms such as "a plurality," "one or more," or "at least one;" however, the absence of such terms is not intended to mean, and should not be interpreted to mean, that a plurality is not conceived.

The term "about" or "approximately," when used before a numerical designation or range (e.g., to define a length or pressure), indicates approximations which may vary by (+) or (−) 5%, 1% or 0.1%. All numerical ranges provided herein are inclusive of the stated start and end numbers. The term "substantially" indicates mostly (i.e., greater than 50%) or essentially all of a device, substance, or composition.

As used herein, the term "comprising" or "comprises" is intended to mean that the devices, systems, and methods include the recited elements, and may additionally include any other elements. "Consisting essentially of" shall mean that the devices, systems, and methods include the recited elements and exclude other elements of essential significance to the combination for the stated purpose. Thus, a system or method consisting essentially of the elements as defined herein would not exclude other materials, features, or steps that do not materially affect the basic and novel characteristic(s) of the claimed invention. "Consisting of" shall mean that the devices, systems, and methods include the recited elements and exclude anything more than a trivial or inconsequential element or step. Embodiments defined by each of these transitional terms are within the scope of this disclosure.

The examples and illustrations included herein show, by way of illustration and not of limitation, specific embodiments in which the subject matter may be practiced. Other embodiments may be utilized and derived therefrom, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. An implant delivery system for controllably deploying an expandable partitioning device in a ventricle of a patient, the implant delivery system comprising:
   a delivery catheter having a proximal end, a distal end, and a tubular shaft therebetween;
   an expandable device comprising a support frame having a plurality of radially expandable resilient ribs connected at their distal ends to a central hub, and a membrane coupled to said ribs;
   a suture extending around a periphery of the membrane, the suture being adapted to be loosened to expand a perimeter region of the expandable device to secure the expandable device in the ventricle of the patient;
   an expansion member near the distal end of the delivery catheter configured to apply pressure to a distal region of the support frame of the expandable device to expand the distal region of the support frame; and
   a coupling element configured to secure the expansion member to the expandable device during deployment;
   wherein the suture is adapted to be tightened to contract the expandable device and to be loosened to permit the expandable device to expand;
   at least one end of the suture extends through the tubular shaft and out the proximal end of the delivery catheter; and
   the expandable device comprises a foot for contacting a first interior wall portion of a heart.

2. The delivery system as defined in claim 1, wherein the suture is removable from the membrane.

3. The delivery system as defined in claim 1, wherein the expansion member is an inflatable balloon.

4. The delivery system as defined in claim 1, wherein ends of the suture are secured together.

5. The delivery system as defined in claim 1, wherein the system comprises a diagnostic instrument integrated into the delivery system to measure hemodynamics of the ventricle during positioning of the expandable device in the heart.

6. An implant delivery system for controllably deploying an expandable device in a ventricle of a patient, the implant delivery system comprising:
   a delivery catheter having a proximal end, a distal end, and a tubular shaft therebetween;
   an expandable device comprising a support frame having radially expandable ribs connected at their distal ends to a central hub, and a membrane coupled to said ribs, wherein said ribs are adapted to anchor to a wall of the ventricle of a heart of the patient; and
   a suture extending around a periphery of the membrane, the suture being adapted to be loosened to expand a perimeter region of the expandable device to secure the expandable device in the ventricle of the patient;
   wherein at least one end of the suture extends through the tubular shaft and out the proximal end of the delivery catheter; and
   wherein the suture is adapted to be tightened to contract the expandable device.

7. An implant delivery system as defined in claim 6, wherein the support frame is self-expanding.

8. A delivery system as defined in claim 7, wherein the suture is adapted to releasably restrain expansion of the expandable device.

9. A delivery system as defined in claim 6, wherein the system further comprises an implant expansion member near the distal end of the delivery catheter configured to apply pressure to a distal region of the support frame of the expandable device to expand the distal region of the support frame; and
   a coupling element configured to secure the expansion member to the expandable device during deployment.

10. An implant delivery system for controllably deploying an expandable device in a ventricle or left atrial appendage of a patient, the implant delivery system comprising:
    a delivery catheter having a proximal end, a distal end, and a tubular shaft therebetween;
    an expandable device comprising a support frame and a membrane coupled to the support frame; and
    a strand extending around a periphery of the membrane, the strand being adapted to be loosened to permit a perimeter region of the expandable device to expand to secure the expandable device against a wall in a portion of a heart of the patient; and
    wherein the strand is adapted to be tightened to contract the expandable device.

11. The delivery system as defined in claim 10, wherein the strand is removable from the membrane.

12. The delivery system as defined in claim 10, wherein the strand is a suture.

13. The delivery system as defined in claim 10, wherein the membrane is impermeable to blood.

14. The delivery system as defined in claim 10, where the system further comprises an expansion member near the distal end of the delivery catheter configured to apply pressure to a distal region of the support frame of the expandable device to expand the distal region of the support frame, the strand being near a proximal region of the support frame.

15. The delivery system as defined in claim 14, further comprising a coupling element configured to secure the expansion member to the expandable device during deployment.

16. The delivery system as defined in claim 10, wherein the support frame is self-expanding.

17. The delivery system as defined in claim 10, wherein an end of the strand is adapted to be pulled to remove the strand from the periphery of the membrane.

18. The delivery system as defined in claim 10, wherein the system includes a hypotube on the distal end of the delivery catheter, at least one end of the strand extending into the hypotube.

19. The delivery system as defined in claim 18, wherein the hypotube comprises a slot for receiving the strand of the expandable device.

20. The delivery system as defined in claim 10, wherein at least one end of the strand extends through the tubular shaft and out the proximal end of the delivery catheter.

21. The delivery system as defined in claim 10, wherein both ends of the strand are threaded through the tubular shaft of the delivery catheter.

22. The delivery system as defined in claim 10, further comprising means to loosen the strand about the membrane to permit the expandable device to expand.

23. The delivery system as defined in claim 10, further comprising means to tighten the strand about the membrane to permit the expandable device to contract.

24. The delivery system of claim 10, wherein the system includes a clamp on the distal end of the delivery catheter, at least one end of the strand being secured to the clamp.

25. The delivery system as defined in claim 10, wherein the support frame of the expandable device comprises a plurality of radially expandable resilient ribs connected at their distal ends to a central hub, and the membrane is coupled to said ribs, wherein said ribs are adapted to anchor to the wall of the ventricle of the heart to store energy provided by said ventricle during systole and to provide an elastic recoil force to said wall of said ventricle during diastole.

26. The delivery system as defined in claim 10, further comprising a diagnostic instrument integrated into the delivery system that measures hemodynamics in the heart.

27. The delivery system as defined in claim 10, wherein the expandable device is a ventricle portioning device.

28. The delivery system as defined in claim 10, wherein the expandable device is a device to seal the left atrial appendage.

29. A method for controllably deploying an expandable device in a ventricle of a patient, the method comprising:
   positioning the expandable device in the ventricle of the patient;
   deploying an expansion member, near a distal end of a delivery catheter of a delivery system, coupled to the expandable device to apply pressure to a region of a support frame of the expandable device, wherein applying pressure to the region of the support frame expands the region of the support frame;
   reducing a volume of the ventricle by partitioning the ventricle into a first region that pumps blood and a second region that does not pump blood; and
   controllably releasing an end of a suture coupled to the expandable device to secure the expandable device in the ventricle of the patient, wherein controllably releasing the end of the suture causes increased outward expansive force of the expandable device and securing the expandable device against a wall of the ventricle.

30. The method of claim 29, wherein deploying and releasing occur simultaneously.

31. The method of claim 29, wherein a diagnostic instrument is integrated into the delivery system and the method further comprises measuring hemodynamics in the ventricle.

32. The method of claim 29, wherein the expansion member applies pressure to a distal region of the expandable device and the suture controls expansion of a proximal region of the expandable device.

33. A method of monitoring blood flow dynamics in a ventricle during positioning of an expandable device in the ventricle, the method comprising:
   measuring baseline hemodynamics;
   positioning the expandable device in the ventricle;
   measuring a second set of hemodynamics in the ventricle; and
   repositioning the expandable device based on the hemodynamic measurements.

34. The method of claim 33, wherein the expandable device includes a support frame having a plurality of radially expandable resilient ribs connected at their distal ends to a central hub, and a membrane coupled to the radially expandable resilient ribs.

35. The method of claim 34, wherein a strand extends around a periphery of the membrane and is adapted to be loosened to expand a perimeter region of the expandable device to secure the expandable device in the ventricle.

36. The method of claim 35, wherein repositioning the expandable device includes tightening the strand to contract the expandable device.

37. The method of claim 33, wherein a diagnostic instrument is integrated into a delivery system for the expandable device, and the diagnostic instrument measures one or more of the baseline hemodynamics or the second set of hemodynamics.

* * * * *